US007790866B2

(12) United States Patent
Ohara et al.

(10) Patent No.: US 7,790,866 B2
(45) Date of Patent: Sep. 7, 2010

(54) CANCER-ASSOCIATED GENE

(75) Inventors: Osamu Ohara, Chiba (JP); Takahiro Nagase, Chiba (JP); Reiko Kikuno, Chiba (JP); Shin-ichi Funahashi, Ibaraki (JP)

(73) Assignees: Chugai Seiyaku Kabushiki Kaisha, Tokyo (JP); Kazusa DNA Research Institute, Kisarazu-shi (JP)

( * ) Notice: Subject to any disclaimer, the term of this patent is extended or adjusted under 35 U.S.C. 154(b) by 12 days.

(21) Appl. No.: 10/535,733

(22) PCT Filed: Nov. 20, 2003

(86) PCT No.: PCT/JP03/14812

§ 371 (c)(1), (2), (4) Date: May 20, 2005

(87) PCT Pub. No.: WO2004/046358

PCT Pub. Date: Jun. 3, 2004

(65) Prior Publication Data

US 2006/0275302 A1 Dec. 7, 2006

(30) Foreign Application Priority Data

Nov. 21, 2002 (JP) ............................ 2002-338549

(51) Int. Cl.

*C07H 21/02* (2006.01)
*C07H 21/04* (2006.01)
*C07K 14/00* (2006.01)
*C07K 17/00* (2006.01)
*C12P 21/06* (2006.01)
*C12P 19/34* (2006.01)
*C12N 15/64* (2006.01)

(52) U.S. Cl. ..................... 536/23.1; 536/23.5; 530/350; 435/69.1; 435/91.1; 435/91.4

(58) Field of Classification Search ....................... None
See application file for complete search history.

(56) References Cited

FOREIGN PATENT DOCUMENTS

WO WO-00/08171 A 2/2000
WO WO-02/46426 A2 6/2002
WO WO0246426 A2 * 6/2002
WO WO 0246426 A2 * 6/2002
WO WO-2004/074461 9/2004

OTHER PUBLICATIONS

Lewn, B., et al. Genes IV. 1990. Oxford University Press. p. 810.*

Burgess, W.H., Shaheen, A.M., Ravera, M., Jaye, M., Donohue, P.J., and Winkles, J.A. Possible dissociation of the heparin-binding and mitogenic activities of heparin-binding (acidic fibroblast) growth factor-1 from its receptor-binding activities by site-directed mutagenesis of a single lysine residue. 1990. Jrnl of Cell Biol, vol. 111 p. 2129-38.*

Lazar, E., Watanabe, S., Dalton, S., and Sporn, M.B. Transforming growth factor a: mutation of apartic acid 47 and leucine 48 results in different biological activites. 1988. Molecular and Cellular Biology, vol. 8 No. 3, pp. 1247-1252.*

Schwartz, G.P., Burke, G.T., and Katsoyannis, P.G. A superactive insulin: [B10-Aspartic acid]insulin(human). 1987. Proceedings of the National Academy Sciences, vol. 84, pp. 6408-6411.*

Lin, M.C., Wirght, D.E., Hruby, V.J., and Rodbell, M. Structure-function relationships in glucagon: properties of highly purified Des-His- Monoiodi-, and [Des-Asn28,Thr29](homoserine lactone 27)-glucagon. 1975. Biochemistry, vol. 14 No. 8, pp. 1559-1563.*

Skolnick and Fetrow. From genes to protein structure and function: novel applications of computational approaches in the genomic era. Trends in Biotechnology, 2000. vol. 18, pp. 34-39.*

M. Demetriou et al., *The Journal of Cell Biology*, vol. 130, No. 2, Jul. 1995, 383-392.

M. Granovsky et al., *Nature Medicine*, vol. 6, No. 3, Mar. 2000, 306-312.

K. Murata et al., *Clinical Cancer Research*, vol. 6, 1772-1777, May 2000.

Inamori Kei-Ichiro et al., "Molecular cloning and characterization of human gnT-IX, a novel β1, 6-N-Acetylglucosaminyltransferase that is specifically expressed in the brain" Journal of Biological Chemistry, vol. 278, No. 44, 43102-43109, Oct. 31, 2003. XP002353926.

* cited by examiner

*Primary Examiner*—Larry R. Helms
*Assistant Examiner*—Anne M. Gussow
(74) *Attorney, Agent, or Firm*—Birch, Stewart, Kolasch & Birch, LLP

(57) ABSTRACT

The present invention provides: a novel DNA, a carcinoma-associated gene comprising the DNA, a recombinant protein encoded by the DNA, an antibody binding to the protein, an anti-carcinoma agent comprising the antibody, a low-molecular-weight compound binding to the protein, and a screening system. An example of such a novel DNA is a DNA comprising a nucleotide sequence encoding the following polypeptide (a) or (b):

(a) a polypeptide, consisting of an amino acid sequence identical to or substantially identical to the amino acid sequence represented by SEQ ID NO: 2; or (b) a polypeptide, consisting of an amino acid sequence derived from the amino acid sequence represented by SEQ ID NO: 2 by deletion, substitution, or addition of one or a plurality of amino acids and having biological activity substantially equivalent to the functions of the polypeptide (a).

5 Claims, 3 Drawing Sheets

Anti-FJ04470 peptide polyclonal antibody

```
           580                                                      629
FJ04470    SQHPYAENFI GKPHVWTVDY NNSEEFEAAI KAIMRTQVDP YLPYEYTCEG
GnT-V      SQHPYAEVFI GRPHVWTVDL NNQEEVEDAV KAILNQKIEP YMPYEFTCEG
Consensus  SQHPYAE-FI G-PHVWTVD- NN-EE-E-A- KAI------P Y-PYE-TCEG
           630                                                      679
FJ04470    MLERIHAYIQ HQDFCRAPDP ALPEAHAPQS PFVLAPNATH LEWARNTSLA
GnT-V      MLQRINAFIE KQDFC..... .....HGQ.. ..VM...... ..........
Consensus  ML-RI-A-I- -QDFC----- -----H---- --V------- ----------
           680                                                      729
FJ04470    PGAWPPAHAL RAWLAVPGRA CTDTCLDHGL ICEPSFFPFL NSQDAFLKLQ
GnT-V      ...WPPLSAL QVKLAEPGQS CKQVCQESQL ICEPSFFQHL NKDKDMLKYK
Consensus  ---WPP--AL ---LA-PG-- C---C----L ICEPSFF--L N-----LK--
           730                                                      779
FJ04470    VPCDSTESEM NHLYPAFAQP GQECYLQKEP LLFSCAGSNT KYRRLCPCRD
GnT-V      VTCQSSELAK DILVPSFDPK NKHCVFQGDL LLFSCAGAHP RHQRVCPCRD
Consensus  V-C-S-E--- --L-P-F--- ---C--Q--- LLFSCAG--- ---R-CPCRD
           780        792
FJ04470    FRKGQVALGQ GCL
GnT-V      FIKGQVALCK DCL
Consensus  F-KGQVAL-- -CL
```

| | | | |
|---|---|---|---|
| ① | RA1 030121 | ② | RA1 030225 |
| ③ | RA2 030121 | ④ | RA2 030225 |
| ⑤ | AG1 030121 | ⑥ | AG1 030225 |
| ⑦ | AG2 030121 | ⑧ | AG2 030225 |

CANCER-ASSOCIATED GENE

TECHNICAL FIELD

The present invention relates to a novel DNA, a carcinoma-associated gene comprising the DNA, a recombinant protein encoded by the DNA, an antibody binding to the protein, an anti-carcinoma agent comprising the antibody, a low-molecular-weight compound binding to the protein, a screening system, an antisense DNA, and an siRNA.

BACKGROUND ART

Information concerning the nucleotide sequences of the human genome is produced everyday by large-scale sequencing in the human genome project. The final object of the human genome project is not simply to determine the entirety of the nucleotide sequences of the genome, but also to elucidate the constitutional information thereof; that is, information about various human life phenomena from the nucleotide sequence information of DNA. Regions encoding proteins in the human genome sequences account for only a small portion thereof. Currently, prediction of coding regions is being carried out using information science techniques that are referred to as "neural network" and using the hidden Markov model. However, the prediction accuracies of these techniques are not yet sufficient. Even under the current situation, where information concerning the nucleotide sequences of the human genome has been accumulated, coding regions are still being elucidated. Moreover, elucidation of the functions of a protein that is encoded by each coding region is a future object. In the future, for example, it is desired to analyze a gene associated with a specific disease such as carcinoma and to utilize such gene for the detection and treatment of carcinoma.

For example, it has been conventionally reported that N-type sugar chains of glycoproteins are associated with carcinoma. The N-type sugar chains of glycoproteins are involved in various life phenomena, fertilization, generation, immunology, intracellular transport, aging, carcinoma, and the like, so that various pathological conditions are induced by abnormal sugar chains. In particular, high branching of sugar chains is observed in carcinoma cells, indicating their involvement in biological activity such as the metastasis ability of carcinoma cells. The formation of a high-branched sugar chain structure is determined by activation of a specific glycosyltransferase. N-acetylglucosamin transferase is known as an enzyme important in determination of a sugar chain structure. N-acetylglucosamin transferase I and II (GnT-I and -II) are involved in determination of a basic core structure. Each of GnT-III, -IV, -V, and -VI enzymes is involved in transferring N-acetylglucosamin to a particular part of a sugar chain, thus having a large effect on high branching. Furthermore, sialic acid transferase and fucose transferase are enzymes important in determination of the terminal structures of a sugar chain.

Although GnT-III, -IV, -V, and -VI recognize a common substrate, almost no homology was found in the cDNA structures thereof. GnT-III acts to transfer N-acetylglucosamin to a mannose of the core of a N-type binding sugar chain, forming double-branched GlcNAc. GnT-IV and -VI are enzymes involved in biosynthesis of β1-4 chain of N-glycan. GnT-V is an enzyme involved in biosynthesis of β1-6 chain of N-glycan. An example of such an N-acetylglucosamine transferase associated with canceration is GnT-V.

Association of GnT-V with metastasis has been reported (see non-patent document 1 and non-patent document 2). Granovsky et al. have shown that in an experiment using GnT-V-knockout mice, GnT-V is also essential in carcinoma growth in addition to metastasis. Furthermore, Murata et al. have reported correlation between GnT-V and metastasis of colon carcinoma (see non-patent document 3).

Non-patent document 1

Demetriou M et al., J. Cell Biol., 130 (1995), 383

Non-patent document 2

Granovsky et al., Nat. Med., 6 (2000), 306

Non-patent document 3

Murata et al., Clin. Cancer Res., 6 (2000), 1772

SUMMARY OF THE INVENTION

An object of the present invention is to provide a novel gene associated with carcinoma; that is, a novel gene associated with GnT-V by obtaining a full-length cDNA from human-derived cDNA libraries. Furthermore, objects of the present invention are to provide a method for detecting carcinoma using a fragment of the novel gene, a protein encoded by the novel gene, an antibody against the protein, an anti-carcinoma agent comprising the antibody, and a method for screening for a substance binding to the above protein.

To discover a novel gene, the present inventors have succeeded at this time in direct cloning of novel DNAs comprising regions encoding proteins from cDNA libraries derived from the human adult whole brain, human tonsil, human hippocampus, and human fetal whole brain, so that they have determined the nucleotide sequences thereof and thus have completed the present invention.

The present invention relates to a gene encoding a protein showing 44% homology with GnT-V, which is thought to be a novel glycosyltransferase. High-level expression of the gene is observed in carcinoma cells, particularly in lung carcinoma, breast carcinoma, prostatic adenocarcinoma, and pancreatic carcinoma cell lines. Thus, the gene is inferred to be a gene relating to these types of carcinoma. Although it has been reported that GnT-V is involved in metastasis of colon carcinoma and the expression thereof is observed also in colon carcinoma cell lines, the expression of the gene of the present invention is not observed in colon carcinoma cell lines. However, the expression of the gene of the present invention is observed in SW620 cells that are of a cell line obtained in the case of metastasis of colon carcinoma to the lymph node, suggesting that the gene is also involved in metastasis.

Therefore, the present invention is useful in diagnosis, treatment, and prevention of carcinoma, particularly lung carcinoma, breast carcinoma, prostatic adenocarcinoma, and pancreatic carcinoma, and in diagnosis concerning metastasis.

That is, a first aspect of the present invention relates to a DNA comprising a nucleotide sequence encoding the following polypeptide (a) or (b):

(a) a polypeptide, consisting of an amino acid sequence identical to or substantially identical to the amino acid sequence represented by SEQ ID NO: 2; or (b) a polypeptide, consisting of an amino acid sequence derived from the amino acid sequence represented by SEQ ID NO: 2 by deletion, substitution, or addition of one or more amino acids composing a portion of the amino acid sequence and having biological activity substantially equivalent to the functions of the polypeptide (a).

A second aspect of the present invention relates to the following DNA (a) or (b):

(a) a DNA, comprising the nucleotide sequence represented by SEQ ID NO: 1 and comprising the nucleotide sequence that encodes the amino acid sequence represented by SEQ ID NO: 2; or (b) a DNA, hybridizing under stringent conditions to the DNA (a) and encoding a protein having biological activity substantially equivalent to the functions of a polypeptide comprising the amino acid sequence in (a).

Hereinafter, the above DNAs according to the first and the second aspects of the present invention are together referred to as "the DNA of the present invention." In addition, the present invention also relates to genes comprising such DNAs.

A third aspect of the present invention relates to a protein comprising the following polypeptide (a) or (b):

(a) a polypeptide, consisting of an amino acid sequence identical to or substantially identical to the amino acid sequence represented by SEQ ID NO: 2; or (b) a polypeptide, consisting of an amino acid sequence derived from the amino acid sequence represented by SEQ ID NO: 2 by deletion, substitution, or addition of one or more amino acids composing a portion of the amino acid sequence and having biological activity substantially equivalent to the functions of the polypeptide (a); and a recombinant protein obtained by causing the expression of the gene of the present invention.

Furthermore, a fourth aspect of the present invention relates to various antibodies binding to the above protein.

Furthermore, a fifth aspect of the present invention relates to various anti-carcinoma agents comprising antibodies.

Furthermore, a sixth aspect of the present invention relates to a method for screening for a substance binding to the above protein or a partial peptide thereof, comprising the steps of:

(a) bringing a test sample into contact with the protein or a partial peptide thereof;

(b) detecting binding activity of the protein or the partial peptide thereof with the test sample; and (c) selecting a compound having activity to bind to the protein or the partial peptide thereof.

Furthermore, a seventh aspect of the present invention relates to a polynucleotide hybridizing under stringent conditions to the DNA of the present invention and consisting of at least 15 nucleotides.

Furthermore, an eighth aspect of the present invention relates to a method for detecting carcinoma using the above polynucleotide as a probe, comprising the steps of:

(a) bringing a test sample into contact with the polynucleotide; and (b) detecting activity of hybridization between the polynucleotide and the test sample.

1. Obtainment of DNA of the Present Invention

A DNA of the present invention is obtained by isolation as a cDNA fragment from cDNA libraries prepared by the present inventors using as starter materials mRNAs of commercial (Clontech) human adult whole brain, human tonsil, human hippocampus, and human fetal whole brain and determining and identifying the nucleotide sequences thereof.

That is, specifically, clones are randomly isolated from cDNA libraries derived from human adult whole brain, human tonsil, human hippocampus, and human fetal whole brain, which are prepared according to Ohara et al's method (DNA Research Vol.4, 53-59 (1997)).

Next, through hybridization, duplicated clones (which appear repeatedly) are removed and then in vitro transcription and translation are carried out. Nucleotide sequences of both termini of clones, for which products of 50 kDa or more are confirmed, are determined.

Furthermore, databases of known genes are searched for homology using the thus obtained terminal nucleotide sequences as queries. The entire nucleotide sequence of a clone revealed to be novel as a result is determined.

In addition to the above screening method, the 5' and 3' terminal sequences of cDNA are related to a human genome sequence. Then an unknown long-chain gene is confirmed in a region between the sequences, and the full-length of the cDNA is analyzed.

In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences.

As described above, a clone (FJ04470) having a DNA of the present invention can be obtained. Functions and the like of a protein of the present invention encoded by a gene contained in the clone are shown in this specification.

In another means for cloning a DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention.

Hybridization can be carried out by, for example, the method described in the above Current Protocols in Molecular Biology (edited by Frederick M. Ausubel et al., 1987). In addition, when a commercial library is used, hybridization can be carried out according to a method described in the attached instructions.

A DNA of the present invention may be any DNA, as long as it contains a nucleotide sequence encoding the polypeptide of the present invention as described above. Such a DNA may be a cDNA identified and isolated from cDNA libraries or the like that are derived from human brain or tissues other than the human brain (for example, cells and tissues such as those taken from the heart, lung, liver, spleen, kidney, or testis). Such a DNA may also be a synthetic DNA or the like.

Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

2. Polypeptide of the Present Invention

An amino acid sequence substantially identical to the amino acid sequence represented by SEQ ID NO: 2 means an amino acid sequence having a degree of homology with the entire amino acid sequence represented by SEQ ID NO: 2, such as an overall mean homology of approximately 70% or more, preferably approximately 80% or more, further preferably approximately 90% or more, and particularly preferably approximately 95% or more. Numerical values of homology described in this specification may be calculated using a homology search program known by persons skilled in the art, such as BLAST (J. Mol. Biol., 215, 403-410 (1990)) and FASTA (Methods. Enzymol., 183, 63-98 (1990)), unless they are particularly specified. Preferably, such numerical values are calculated using default (initial setting) parameters in BLAST or using default (initial setting) parameters in FASTA.

Therefore, for example, the polypeptide consisting of an amino acid sequence substantially identical to the amino acid sequence represented by SEQ ID NO: 2 of the present invention is a polypeptide having the above homology with the amino acid sequence represented by SEQ ID NO: 2 and having biological activity (functions) substantially equivalent to the functions of the polypeptide consisting of the amino acid sequence represented by SEQ ID NO: 2. Here, "substantially equivalent" means that the activity (functions) of such a polypeptide is characteristically the same as that of the other. The activity level (high or low) is not limited, but is preferably 50% or more, more preferably 60% or more, further preferably 70% or more, and particularly preferably 80% or more of the activity of the protein having the amino acid sequence represented by SEQ ID NO: 2. An example of the biological activity of a protein of the present invention is activity to transfer a sugar to a polypeptide. The biological activity of a protein of the present invention may be determined by measuring glycosyltransferase activity as described in a known document (for example, Cell Technology, separate volume, Glycobiology Experimental Protocol, Shujunsha, supervised by Naoyuki Taniguchi et al., 1996).

Furthermore, examples of the polypeptide of the present invention also include a polypeptide consisting of an amino acid sequence derived from the amino acid sequence represented by SEQ ID NO: 2 by deletion, substitution, or addition or a combination thereof of one or a plurality of (preferably within 1 to 20, more preferably within 1 to 10, and further preferably within 1 to 5) amino acids, and having biological activity (functions) substantially equivalent to the functions of the polypeptide consisting of the amino acid sequence represented by SEQ ID NO: 2.

3. DNA of the Present Invention

A DNA encoding the above polypeptide consisting of an amino acid sequence that is substantially identical to the amino acid sequence represented by SEQ ID NO: 2 or a DNA encoding the above polypeptide consisting of an amino acid sequence derived from the amino acid sequence represented by SEQ ID NO: 2 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art.

In addition, at this time, a possible method for causing a polypeptide to have substantially equivalent biological activity is substitution of homologous amino acids (e.g., polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in each polypeptide of the present invention are preferably conserved.

Furthermore, examples of a DNA of the present invention include a DNA comprising the nucleotide sequence represented by SEQ ID NO: 1 and comprising the nucleotide sequence that encodes the amino acid sequence represented by SEQ ID NO: 2 and a DNA hybridizing under stringent conditions to the DNA and encoding a polypeptide (protein) having biological activity (functions) equivalent to the functions of the polypeptide consisting of the amino acid sequence represented by SEQ ID NO: 2.

Under such conditions, an example of such a DNA capable of hybridizing to the DNA comprising the nucleotide sequence represented by SEQ ID NO: 1 and comprising the nucleotide sequence that encodes the amino acid sequence represented by SEQ ID NO: 2 is a DNA comprising a nucleotide sequence that has a degree of overall mean homology with the entire nucleotide sequence of the DNA, such as approximately 80% or more, preferably approximately 90% or more, and more preferably approximately 95% or more.

Hybridization can be carried out according to a method known in the art such as a method described in Current Protocols in Molecular Biology (edited by Frederick M. Ausubel et al., 1987)) or a method according thereto. In addition, when a commercial library is used, hybridization can be carried out according to a method described in the attached instructions.

Here, "stringent conditions" are, for example, conditions of approximately "1×SSC, 0.1% SDS, and 37° C.," more stringent conditions of approximately "0.5×SSC, 0.1% SDS, and 42° C.," or even more stringent conditions of approximately "0.2×SSC, 0.1% SDS, and 65° C." With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

4. Polynucleotide of the Present Invention

A DNA (gene) of the present invention is expressed in carcinoma cells at high levels as shown in the following examples, so that the detection of the gene of the present invention can be utilized for the detection of carcinoma.

Therefore, a polynucleotide hybridizing under stringent conditions to a DNA of the present invention containing the nucleotide sequence represented by SEQ ID NO: 1 can be used as a probe in such carcinoma examination. The length of such a polynucleotide is at least 15 nucleotides or more, preferably 100 nucleotides or more, further preferably 500 nucleotides or more, and particularly preferably 1000 nucleotides or more. In addition, such a polynucleotide can also be utilized as a primer for amplifying a gene of the present invention.

For example, through Northern hybridization or RT-PCR using these nucleotides as probes or primers, abnormal expression of a gene encoding a protein of the present invention can be examined. Furthermore, through PCR using these nucleotides as primers, the gene, DNA, or mRNA encoding the protein of the present invention is amplified and then abnormal expression of the gene can be examined and diagnosed by a method such as RFLP analysis, SSCP, or sequencing.

When nucleotides are used as a primer, a chain length thereof is generally between 15 and 100 nucleotides and preferably between 15 and 35 nucleotides. When used as a probe, nucleotides with a chain length of at least 15 nucleotides containing at least a portion or the entire sequence of a DNA of the present invention are used. Such nucleotides preferably hybridize specifically to a DNA encoding a protein of the present invention. "Specifically hybridize" means to hybridize to the DNA (SEQ ID NO: 1) encoding the protein of the present invention under general hybridization conditions and preferably under stringent conditions, but not to hybridize to DNAs encoding other proteins.

Here, "stringent conditions" are, for example, conditions of approximately "1×SSC, 0.1% SDS, and 37° C.," more stringent conditions of approximately "0.5×SSC, 0.1% SDS, and 42° C.," or even more stringent conditions of approximately "0.2×SSC, 0.1% SDS, and 65° C." With more stringent hybridization conditions, the isolation and detection of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

Specifically, a polynucleotide hybridizing under stringent conditions to a DNA of the present invention and consisting of at least 15 nucleotides is brought into contact with a test sample inferred to contain the DNA of the present invention and then activity of hybridization between the above polynucleotide and the test sample is detected, so that whether or not a subject, the origin of the test sample, is affected with carcinoma can be detected. Hybridization activity is detected in a case when a DNA or a fragment thereof capable of hybridizing to the above polynucleotide is present in the test sample.

At this time, the gene of the present invention can be specifically detected by the use of a polynucleotide encoding a portion exhibiting low homology when a protein of the present invention and a protein (the two proteins share high homology in terms of amino acid sequence) are compared and consisting of at least 15 nucleotides. For example, GnT-V and a protein of the present invention are compared in terms of amino acid sequence, and then a polynucleotide encoding a portion with low homology is used. Specific examples of such a polynucleotide include the polynucleotide encoding the amino acid sequence represented by SEQ ID NO: 3 or 4 and a fragment thereof consisting of at least 15 nucleotides.

By the use of a DNA of the present invention or a gene containing the DNA as a probe, the above gene diagnosis using the DNA of the present invention can be carried out by, for example, known Northern hybridization or a PCR-SSCP method (Genomics, Vol. 5, pp. 874-879 (1989); Proceedings of the National Academy of Sciences of the United States of America, Vol. 86, pp. 2766-2770 (1989)).

5. Obtainment of Protein of the Present Invention

A protein of the present invention can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

The above expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector.

As vectors, plasmids derived from *Escherichia coli* (e.g., pBR322, pBR325, pUC18, and pUC118), plasmids derived from *Bacillus subtilis* (e.g., pUB110, pTP5, and pC194), plasmids derived from yeast (e.g., pSH19 and pSH15), bacteriophages such as λ phage, and animal viruses such as retrovirus, vaccinia virus, and baculovirus can be utilized.

Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRα promoter, an SV40 promoter, an LTR promoter, a CMV promoter, and an HSV-TK promoter.

In addition to the above, features known in the art, such as an enhancer, a splicing signal, a polyA addition signal, a selection marker, and an SV40 replication origin can be added to an expression vector, if desired. Moreover, if necessary, the protein encoded by a DNA of the present invention can be expressed as a fusion protein with another protein (for example, glutathione S-transferase and protein A). Such a fusion protein can be cleaved using an appropriate protease, and then separated into each protein.

As host cells, for example, bacteria of the genus *Escherichia*, bacteria of the genus *Bacillus*, yeast, insect cells, insects, and animal cells are used.

Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)).

As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used.

As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used.

As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, and human FL cells are used.

Transformation of these host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973).

The thus obtained transformant transformed with an expression vector containing a DNA of the present invention or a gene containing a DNA of the present invention can be cultured according to a method known in the art. For example, documents shown below can be referred to.

For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added.

When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added.

When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

To separate and purify a polypeptide or a protein of the present invention from the above culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods.

The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed.

The presence of a polypeptide (protein) of the present invention or a salt thereof can be measured by various binding assays, enzyme immunoassays using specific antibodies, and the like.

6. Antibody of the Present Invention

An antibody of the present invention is not specifically limited, as long as it binds to a protein of the present invention and can be obtained as a polyclonal or a monoclonal antibody using a known means. As an antibody used in the present invention, a monoclonal antibody derived from a mammal is particularly preferable. Examples of monoclonal antibodies derived from mammals include those produced by hybridomas and those produced by hosts transformed with expression vectors containing antibody genes by gene engineering techniques. In addition, it is preferable that the antibody of the present invention is able to specifically bind to a protein of the present invention.

Monoclonal-antibody-producing hybridomas can be prepared as described below basically using known art. Specifically, a hybridoma can be prepared by performing immunization according to a general immunization method using a protein of the present invention as a sensitizing antigen, fusing the resulting immunocyte with a known parent cell by a general cell fusion method, and then screening for a monoclonal-antibody-producing cell by a general screening method. Specifically, a monoclonal antibody is prepared as described below.

The gene sequence encoding a protein of the present invention is inserted into a known expression vector system to transform an appropriate host cell, and then the target protein of the present invention is purified by a known method from the host cell or the culture supernatant.

Next, the protein of the present invention is used as a sensitizing antigen. Alternatively, a partial peptide of the protein of the present invention can also be used as a sensitizing antigen. At this time, the partial peptide can be obtained by chemical synthesis according to a general method known by persons skilled in the art from the amino acid sequence of the protein of the present invention.

As a partial polypeptide of the protein of the present invention, for example, a peptide having an amino acid sequence of at least 10 or more, preferably 50 or more, further preferably 70 or more, more preferably 100 or more, and most preferably 200 or more amino acids of the amino acid sequence composing the protein of the present invention and having, for example, biological activity substantially equivalent to the functions of a polypeptide of the present invention is used. As a partial polypeptide of the present invention, for example, a polypeptide containing each functional domain described later is particularly preferable. Furthermore, the C-terminus of a partial peptide of the present invention is generally a carboxyl group (—COOH) or carboxylate (—COO—). However, like the above-mentioned protein of the present invention, the C-terminus may be amide (—$CONH_2$) or ester (—COOR). Moreover, similar to the above-mentioned protein of the present invention, examples of a partial peptide of the present invention include a peptide wherein an amino group of the N-terminal methionine residue is protected with a protecting group, a peptide wherein a glutamyl group generated as a result of in vivo cleavage of the N-terminal side is pyroglutamated, a peptide wherein a substituent on the side chain of intramolecular amino acids is protected with an appropriate protecting group, and a conjugated peptide such as a so-called glycopeptide having a sugar chain bound thereto.

An antibody of the present invention can be used for detection, purification, and the like of a protein of the present invention. Furthermore, as shown in the following examples, a gene of the present invention is expressed at high levels in carcinoma cells. Hence, cell growth can be suppressed by binding a cytotoxic substance such as a radioactive isotope, a chemotherapeutant, or a toxin derived from a bacterium to an antibody of the present invention. Accordingly, an epitope on a protein molecule of the present invention, which is recognized by an antibody of the present invention, is not limited to a specific epitope. Any epitope may be recognized, as long as it is present on a protein molecule of the present invention. Therefore, as an antigen for preparing an antibody of the present invention, any fragment can also be used, as long as it contains an epitope that is present on a protein molecule of the present invention.

Furthermore, to obtain an antibody specific to a protein of the present invention, for example, a peptide that composes a portion exhibiting low homology when a protein of the present invention and a protein (the two proteins share high homology in terms of amino acid sequence) are compared and consisting of at least 6 amino acids, preferably 8 amino acids, and further preferably 10 amino acids, is used as an antigen for preparing such an antibody. For example, GnT-V and a protein of the present invention are compared in terms of amino acid sequence, and a portion with low homology is used. For example, a peptide comprising the amino acid sequence represented by SEQ ID NO: 3 or 4 or a fragment thereof comprising at least 6 amino acids can be used.

An antibody of the present invention recognizes and binds to an antigen for use in preparation of the above antibody. This antibody can be obtained by administering the above antigen to an animal. Moreover, such an antibody can also be obtained by affinity chromatography using the above antigen from a polyclonal antibody obtained by administering a protein of the present invention to an animal. Furthermore, such an antibody can also be obtained by screening for a hybridoma producing an antibody that binds to the above antigen from among many monoclonal-antibody-producing hybridomas.

Mammals to be immunized with sensitizing antigens are not specifically limited and are preferably selected taking into consideration their compatibility with parent cells to be used for cell fusion. In general, rodents, such as mice, rats, and hamsters, are used.

An animal is immunized with a sensitizing antigen according to a known method. For example, as a general method, a sensitizing antigen is injected intraperitoneally or subcutaneously into a mammal. Specifically, a sensitizing antigen is diluted or suspended in an appropriate amount using PBS (Phosphate-Buffered Saline), physiological saline, or the like, a general adjuvant such as a Freund's complete adjuvant is mixed in an appropriate amount with the resultant if desired, and then the resultant is emulsified and administered several times to a mammal every 4 to 21 days. In addition, an appropriate carrier can also be used upon immunization with a sensitizing antigen.

Mammals are immunized as described above, and then a rise in the desired antibody level in the serum is confirmed. Subsequently, immunocytes are collected from the mammals, and then the cells are subjected to cell fusion. A preferred immunocyte is particularly a spleen cell.

As parent cells to be fused with the above immunocytes, mammalian myeloma cells are used. As myeloma cells, cells of various known cell lines, such as P3 (P3×63Ag8.653) (J. Immnol. (1979) 123, 1548-1550), P3×63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133) are preferably used.

The above cell fusion of an immunocyte and a myeloma cell basically can be carried out by a known method, for example, the method of Kohler and Milstein, et al. (Kohler. G. and Milstein, C., Methods Enzymol. (1981) 73, 3-46).

More specifically, the above cell fusion is carried out in a general nutrition culture solution in the presence of, for example, an agent for promoting cell fusion. As an agent for promoting cell fusion, for example, polyethylene glycol (PEG) or Sendai virus (HVJ) is used. To further enhance fusion efficiency if desired, an adjuvant such as dimethylsulfoxide can be additionally used.

The ratio of immunocytes to myeloma cells to be used herein can be arbitrarily determined. For example, myeloma cells and immunocytes may be used preferably at a ratio ranging from 1:1 to 1:10. As a culture solution for use in the above cell fusion, for example, those appropriate for the growth of the above myeloma cell lines, such as an RPMI1640 culture solution and an MEM culture solution, and other culture solutions generally used for this type of cell culture can be used. In addition, a supplemental serum fluid such as fetal calf serum (FCS) can also be used together therewith.

Cell fusion is carried out as follows. The above immunocytes and myeloma cells in predetermined amounts are mixed well in the above culture solution, a PEG solution (for example, one with an average molecular weight between approximately 1000 and 6000) pre-heated to approximately 37° C. is added at a concentration generally between 30% and 60% (w/v) to the solution, and then the solution is mixed, thereby forming target fusion cells (hybridomas). Subsequently, a process of successively adding an appropriate culture solution and centrifuging the solution to remove the supernatant is repeated, so that an agent for cell fusion or the like, which is unfavorable for the growth of hybridomas, is removed.

The thus obtained hybridomas are selected by culturing the hybridomas in a general selection culture solution, such as an HAT culture solution (a culture solution containing hypoxanthine, aminopterin, and thymidine). Culture in the above HAT culture solution is continued for a time (generally several days to several weeks) sufficient for cells (unfused cells) other than target hybridomas to die. Next, a general limiting dilution method is carried out, so that screening for and simple cloning of hybridomas producing target antibodies are performed.

In addition to obtaining the above hybridoma by immunizing a non-human animal with an antigen, a desired human antibody having binding activity to a protein of the present invention can also be obtained by sensitizing in vitro a human lymphocyte with the protein of the present invention. Then the sensitized lymphocyte is fused with a human-derived myeloma cell capable of dividing permanently (see JP Patent Publication (Kokoku) No. 1-59878 B (1989)). Furthermore, a protein of the present invention is administered as an antigen to a transgenic animal having all repertoires of human antibody genes to obtain a cell producing an antibody of the present invention. The cell is immortalized and then a human antibody against the protein of the present invention may also be obtained from the immortalized cell (see International Patent Publication Nos. WO94/25585, WO93/12227, WO92/03918, and WO94/02602).

The thus prepared hybridomas producing monoclonal antibodies can be sub-cultured in general culture solutions, and can be stored for a long time in liquid nitrogen.

To obtain a monoclonal antibody from the hybridoma, a method that involves culturing the hybridoma according to a general method and obtaining the product in the form of a culture supernatant, a method that involves administering the hybridoma to a mammal having compatibility therewith to grow the hybridoma, and then obtaining the product in the form of the ascites of the mammal, or the like is employed. The former method is suitable for obtaining high-purity antibodies, while the latter method is suitable for mass production of antibodies.

In the present invention, as a monoclonal antibody, a recombinant type that is produced by cloning an antibody gene from a hybridoma, incorporating the gene into an appropriate vector, introducing the vector into a host, and then causing the production of the recombinant type using gene recombination techniques can be used (For example, see Vandamme, A. M. et al., Eur. J. Biochem. (1990) 192, 767-775, 1990).

Specifically, mRNA encoding a variable (V) region of an antibody of the present invention is isolated from a hybridoma producing the antibody of the present invention. A mRNA is isolated by a known method, such as a guanidine ultracentrifugation method (Chirgwin, J. M. et al., Biochemistry (1979) 18, 5294-5299) or an AGPC method (Choniczynski, P. et al., Anal. Biochem. (1987) 162, 156-159) to prepare total RNA. Target mRNA is then prepared using an mRNA Purification Kit (produced by Pharmacia) or the like. mRNA can also be directly prepared using a QuickPrep mRNA Purification Kit (produced by Pharmacia).

The cDNA of the antibody V region is synthesized from the obtained mRNA using a reverse transcriptase. A cDNA is synthesized using an AMV Reverse Transcriptase First-strand cDNA Synthesis Kit (produced by SEIKAGAKU CORPORATION), or the like. In addition, to synthesize and amplify a cDNA, for example, a 5'-RACE method using a 5'-Ampli FINDER RACE Kit (produced by Clontech) and PCR (Frohman, M. A. et al., Proc. Natl. Acad. Sci. U.S.A. (1988) 85, 8998-9002; Belyavsky, A. et al., Nucleic Acids Res. (1989) 17, 2919-2932) or the like can be employed.

A target DNA fragment is purified from the obtained PCR product, and then the fragment is ligated to a vector DNA. Furthermore, a recombinant vector is prepared therefrom, the prepared vector is introduced into *Escherichia coli* or the like, and then colonies are selected, so that a desired recombinant vector is prepared. Next, the target DNA nucleotide sequence is confirmed by a known method such as a dideoxynucleotide chain termination method.

After obtainment of the target DNA encoding an antibody V region of the present invention, the DNA is incorporated into an expression vector containing a DNA encoding a desired antibody constant region (C region).

To produce an antibody of the present invention that is used in the present invention, the antibody gene is incorporated into an expression control region of an expression vector, so that the gene is expressed under control of, for example, an enhancer and a promoter. Next, a host cell is transformed using the expression vector for the cell to express the antibody.

For expression of the antibody gene, a host cell may be simultaneously transformed by incorporating a DNA encoding the antibody heavy chain (H chain) and a DNA encoding the antibody light chain (L chain) separately into expression vectors. Alternatively, a host cell may be transformed by incorporating DNA encoding H and L chains into a single expression vector (see WO94/11523).

Furthermore, not only the above host cell, but also a transgenic animal can be used for production of recombinant antibodies. For example, an antibody gene is prepared as a fusion gene by inserting the antibody gene in the middle of a gene encoding a protein (e.g., goat casein) inherently produced in milk. A DNA fragment containing the fusion gene into which the antibody gene has been inserted is injected into a goat embryo, and then the embryo is introduced into female goat. The desired antibody is obtained from milk produced by transgenic goat babies born from goat that has received such embryos or their progeny. Moreover, to increase the volume of milk containing the desired antibody, which is produced by such transgenic goat, hormones may also appropriately be used for the transgenic goat (Ebert, K. M. et al., Bio/Technology (1994) 12, 699-702).

In the present invention, in addition to the above antibody, gene recombinant antibodies that are artificially altered for the purpose of, for example, decreasing heteroantigenicity against humans, such as chimeric antibodies and humanized antibodies, can be used. These modified antibodies can be produced using known methods.

Chimeric antibodies can be obtained by ligating the above-obtained DNA encoding the antibody V region to a DNA encoding a human antibody C region, the resultant is incorporated into expression vectors, and then the vectors are introduced into hosts to produce chimeric antibodies. Chimeric antibodies useful in the present invention can be obtained using such a known method.

A humanized antibody is also referred to as a reshaped human antibody. Such a humanized antibody is prepared by transplanting the complementarity determining region (CDR) of a non-human mammalian antibody, for example, a mouse antibody to the CDR of a human antibody. A general gene recombination technique therefor is also known (see European Patent Application No. EP125023 and WO96/02576).

Specifically, a DNA sequence that is designed so that the CDR of a mouse antibody is ligated to the framework region (FR) of a human antibody is synthesized by the PCR method using as primers several oligonucleotides that have been prepared to have portions overlapping the terminal regions of both CDR and FR (see the method described in WO98/13388).

The framework region of a human antibody, which is selected herein to be ligated via CDR, forms a good antigen-binding site with CDR. If necessary, for the CDR of a reshaped human antibody to form an appropriate antigen-binding site, an amino acid(s) in the FR of the antibody variable region may be substituted (Sato, K. et al., Cancer Res. (1993) 53, 851-856)).

As C regions of a chimeric antibody and a humanized antibody, those of human antibodies are used. For example, in the case of H chain, $C_H1$, $C_H2$, $C_H3$, and $C_H4$, and in the case of L chain, Cκ and Cλ, can be used. In addition, to improve stability of an antibody or the same of the production thereof, a human antibody C region may also be modified.

A chimeric antibody consists of an antibody variable region derived from a non-human mammal and an antibody constant region derived from a human antibody. In the meantime, a humanized antibody consists of the CDR of an antibody derived from a non-human mammal and FR and C regions derived from a human antibody. Antigenicity of a humanized antibody is lowered in a human body, so that it is useful as an active ingredient of a therapeutic agent of the present invention.

Antibodies used in the present invention are not limited to the entirety of the molecules of antibodies and may be fragments of antibodies or modified antibodies, as long as they bind to proteins of the present invention. Divalent and monovalent antibodies may also be included. Examples of fragments of antibodies include Fab, F(ab')2, Fv, Fab/c having one Fab and a complete Fc, single-chain Fv (scFv) having H-chain or L-chain Fv ligated thereto with an appropriate linker, and Diabody. Specifically, antibodies are treated with enzymes such as papain or pepsin to generate antibody fragments, or genes encoding such antibody fragments are constructed, the genes are introduced into expression vectors, and then the genes are expressed in appropriate host cells (for example, see Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 652-663, Rousseaux, J. et al., Methods in Enzymology (1989) 121, 663-669; and Bird, R. E. et al., TIBTECH (1991) 9, 132-137).

scFv is obtained by linking an antibody H-chain V-region and an antibody L-chain V-region. In such scFv, an H-chain V-region and an L-chain V-region are linked via a linker, preferably a peptide linker (Huston, J. S. et al., Proc. Natl. Acad. Sci. U.S.A. (1988) 85, 5879-5883). Such H-chain V-region and L-chain V-region in scFv may be derived from any antibodies described as antibodies in this specification. As a peptide linker for linking V-regions, for example, any single-stranded peptide comprising 12 to 19 amino acid residues is used.

A DNA encoding scFv is obtained as follows. Of the above DNA encoding the H-chain or H-chain V-region of the antibody and a DNA encoding the L-chain or the L-chain V-region of the antibody, the entire DNA sequence thereof or a DNA portion encoding a desired amino acid sequence is used as a template. Amplification is performed by the PCR method using a primer pair that defines both ends. Subsequently, amplification is further performed using in combination a DNA encoding a peptide linker portion and a primer pair that defines both ends so that the H-chain and L-chain are ligated to each of the ends, respectively.

Once a DNA encoding scFv is prepared, an expression vector containing it and a host transformed with the expression vector can be obtained according to standard methods. In addition, scFv can be obtained according to standard methods using the host.

Diabody is prepared by dimerization of two fragments (e.g., scFv), each of which is prepared by linking 2 variable regions with a linker or the like. In general, Diabody contains two VLs and two VHs (e.g., P. Holliger et al., Proc. Natl. Acad. Sci. U.S.A., 90, 6444-6448 (1993); EP404097; WO93/11161; Johnson et al., Method in Enzymology, 203, 88-98, (1991); Holliger et al., Protein Engineering, 9, 299-305, (1996); Perisic et al., Structure, 2, 1217-1226, (1994); John et al., Protein Engineering, 12(7), 597-604, (1999); Holliger et al,. Proc. Natl. Acad. Sci. U.S.A., 90, 6444-6448, (1993); and Atwell et al., Mol. Immunol. 33, 1301-1312, (1996)).

These antibody fragments can be produced in a manner similar to the above. The genes thereof are obtained, they are expressed, and then the fragments are produced by a host. "Antibody" in the present invention encompasses these antibody fragments.

As modified antibodies, antibodies of the present invention that are bound to various molecules such as polyethylene glycol (PEG) can also be used. A radioactive isotope, a chemotherapeutant, a cytotoxic substance such as a toxin derived from a bacterium, or the like can also be bound to an antibody. "Antibody" in the present invention also encompasses these modified antibodies. Such modified antibodies can be obtained by chemically modifying the obtained antibodies. In addition, a method for modifying antibodies has already been established in the field.

Furthermore, antibodies used in the present invention may also be bispecific antibodies. A bispecific antibody may have antigen-binding sites that recognize different epitopes on a protein molecule of the present invention, respectively, may recognize a protein of the present invention and another protein, or may have one antigen-binding site that recognizes a protein of the present invention and another antigen-binding site that recognizes a chemotherapeutant or a cytotoxic substance such as a toxin derived from a cell. In this case, a cytotoxic substance is caused to directly act on cells expressing a protein of the present invention to specifically damage tumor cells, so as to allow suppression of the growth of the tumor cells. A bispecific antibody can also be prepared by binding HL pairs of 2 types of antibodies or can also be obtained by fusing hybridomas producing different monoclonal antibodies so as to prepare a bispecific-antibody-producing fusion cell. Moreover, a bispecific antibody can also be prepared by gene engineering techniques.

Antibody genes constructed as described above can be expressed and obtained by known methods. In the case of mammalian cells, a generally-used useful promoter and an antibody gene to be expressed are functionally linked, a polyA signal is functionally bound downstream on the 3' side thereof, and then the gene can be expressed. Examples of a promoter and an enhancer are a human cytomegalovirus immediate early promoter and enhancer.

Further, examples of a promoter and an enhancer that can be used for antibody expression employed in the present invention include viral promoters and enhancers of viruses such as a retrovirus, a polyoma virus, an adenovirus, and simian virus 40 (SV40) or promoters and enhancers derived from mammalian cells such as human elongation factor 1$\alpha$ (HEF1$\alpha$).

When an SV40 promoter and an SV40 enhancer are used, gene expression can be easily carried out by Mulligan et al.'s method (Nature (1979) 277, 108) and when an HEF1$\alpha$ promoter and an HEF1$\alpha$ enhancer are used, gene expression can be easily carried out by Mizushima et al.'s method (Nucleic Acids Res. (1990) 18, 5322).

A replication origin that can be used herein is derived from SV40, a polyoma virus, an adenovirus, a bovine papilloma virus (BPV), or the like. To amplify the number of gene copies in a host cell line, an expression vector can contain, as a selection marker, an aminoglycoside transferase (APH) gene, a thymidine kinase (TK) gene, an *Escherichia coli* xanthine guanine phosphoribosyltransferase (Ecogpt) gene, a dihydrofolate reductase (dhfr) gene, or the like.

In the case of *Escherichia coli*, a useful and generally used promoter, a signal sequence for antibody secretion, and an antibody gene to be expressed are functionally linked, so that the gene can be expressed. Examples of a promoter include a lacz promoter and an araB promoter. When a lacz promoter is used, a gene can be expressed by Ward et al.'s method (Nature (1098) 341, 544-546; FASEB J. (1992) 6, 2422-2427) and when an araB promoter is used, a gene can be expressed by Better et al.'s method (Science (1988) 240, 1041-1043).

As a signal sequence for antibody secretion, when an antibody is produced by *Escherichia coli* periplasm, a pelB signal sequence (Lei, S. P. et al., J. Bacteriol. (1987) 169, 4379) may be used. Subsequently, when an antibody produced by a periplasm is separated, the structure of the antibody is appropriately refolded and then used.

To produce an antibody used in the present invention, any expression system such as an eukaryotic cell or a prokaryotic cell line can be used. Examples of eukaryotic cells include cells of established mammalian cell lines, cells of established insect cell lines, and animal cells such as eukaryotic filamentous bacterial cells and yeast cells. Examples of prokaryotic cells include bacterial cells such as cells of *Escherichia coli*. Preferably, an antibody used in the present invention is expressed in mammalian cells such as CHO, COS, myeloma, BHK, Vero, and HeLa cells.

Next, transformed host cells are cultured in vitro or in vivo so that they produce target antibodies. Host cells are cultured according to known methods. For example, as a culture solution, DMEM, MEM, RPMI1640, IMDM, or the like can be used. A supplemental serum fluid such as fetal calf serum (FCS) can also be used together therewith.

Antibodies that are expressed and produced as described above can be separated from cells or host animals, and then purified to a uniform level. Antibodies used in the present invention can be separated and purified using an affinity column. Examples of a column using a protein A column include Hyper D, POROS, and Sepharose F. F. (produced by Pharmacia). Other separation and purification methods that are employed for general proteins may be employed and are not particularly limited. For example, antibodies can be separated and purified by appropriately selecting and combining a chromatography column other than the above affinity column, a filter, ultrafiltration, salting out, dialyses, or the like (Antibodies A Laboratory Manual. Ed Harlow, David Lane, Cold Spring Harbor Laboratory, 1988).

For measurement of the antigen-binding activity of an antibody used in the present invention (Antibodies A Laboratory Manual. Ed Harlow, David Lane, Cold Spring Harbor Laboratory, 1988), and activity to inhibit ligand receptor binding (Harada, A. et al., International Immunology (1993) 5, 681-690), known means can be employed.

As a method for measuring the antigen-binding activity of an antibody of the present invention, ELISA (enzyme-linked immunosorbent assay), EIA (enzyme immunoassay), RIA (radioimmunoassay), or a fluorescent antibody technique can be employed. For example, when enzyme immunoassay is employed, to a plate coated with a protein of the present invention, a sample containing an antibody of the present invention such as a culture supernatant of a cell producing the antibody of the present invention or the purified antibody is added. A secondary antibody labeled with an enzyme such as alkaline phosphatase is added, the plate is incubated and then washed, an enzyme substrate such as p-nitrophenyl phosphate is added, and then absorbance is measured, so that the antigen-binding activity can be evaluated.

An antibody of the present invention may have cytotoxic activity. Examples of cytotoxic activity in the present invention include complement-dependent cytotoxicity (CDC) activity and antibody-dependent cell-mediated cytotoxicity (ADCC) activity. In the present invention, "CDC activity" means cytotoxic activity of a complement system and "ADCC activity" means activity of damaging a target cell when a specific antibody attaches to a cell surface antigen of the target cell, and then a cell (e.g., immunocyte) having a Fcγ receptor binds to the Fc portion via the Fcγ receptor so as to damage the target cell.

Whether or not an antibody of the present invention has ADCC activity or CDC activity can be measured by a known method (for example, Current protocols in Immunology, Chapter 7. Immunologic studies in humans, Editor, John E, Coligan et al., John Wiley & Sons, Inc., (1993)).

Specifically, for example, cytotoxic activity can be measured by the following methods.

Preparation of Effector Cell

Spleens are excised from CBA/N mice or the like and spleen cells are separated in RPMI1640 media (produced by GIBCO). After washing in the same media containing 10% fetal bovine serum (FBS, produced by HyClone), the cell concentration is prepared at $5\times10^6$/ml, thereby preparing effector cells.

Preparation of Complement Solution

Baby Rabbit Complement (produced by CEDARLANE) was diluted 10-fold in a 10% FBS-containing medium (produced by GIBCO), thereby preparing a complement solution.

Preparation of Target Cell

Cells expressing a protein of the present invention (e.g., prostatic adenocarcinoma cells, ovarian carcinoma cells, or colon carcinoma cells) are cultured at 37° C. for 1 hour in a 10% FBS-containing DMEM medium together with 0.2 mCi of $^{51}$Cr-sodium chromate (produced by Amersham Pharmacia Biotech), so that the cells are radio-labeled. After radio-labeling, the cells are washed 3 times in a 10% FBS-containing RPMI1640 medium, and then the cell concentration is adjusted at $2\times10^5$/ml, thereby preparing target cells.

Measurement of ADCC Activity

The target cells and the antibody of the present invention are added in amounts of 50 μl each to a 96-well U-bottomed plate (produced by Beckton Dickinson), followed by reaction on ice for 15 minutes. Subsequently, 100 μl of the effector cells is added, and the cells are cultured within a carbon dioxide incubator for 4 hours. The final concentration of the antibody is 0 or 10 μg/ml. After culture, 100 μl of the supernatant is collected, and then radioactivity is measured using a gamma counter (COBRAIIAUTO-GMMA, MODEL D5005, produced by Packard Instrument Company). Cytotoxic activity (%) can be found by $(A-C)/(B-C)\times100$. "A" denotes radioactivity (cpm) in each sample, "B" denotes radioactivity (cpm) in a sample to which 1% NP-40 (produced by Nacalai Tesque, Inc.) has been added, and "C" denotes radioactivity (cpm) in a sample containing only the target cells.

Measurement of CDC Activity

The target cells and the antibody of the present invention are added in amounts of 50 μl each to a 96-well flat-bottomed plate (produced by Becton Dickinson), followed by reaction on ice for 15 minutes. Subsequently, 100 μl of the complement solution is added, and the cells are cultured within a carbon dioxide incubator for 4 hours. The final concentration of the antibody is 0 or 3 μg/ml. After culture, 100 μl of the supernatant is collected, and then radioactivity is measured using a gamma counter. Cytotoxic activity can be found in a manner similar to that employed for measurement of ADCC activity.

7. Anti-Carcinoma Agent of the Present Invention

An effective dose of an anti-carcinoma agent (therapeutic agent against carcinoma) of the present invention is selected from a range between 0.001 mg and 1000 mg per kg body weight per administration. Alternatively, a dose can be selected from a range between 0.01 and 100000 mg/body of a patient. However, the dose of a therapeutic agent of the present invention is not limited to these doses. Furthermore, regarding timing for administering a therapeutic agent of the present invention, the agent can be administered either before or after the advent of clinical symptoms of a disease. A therapeutic agent of the present invention can be formulated according to a standard method (Remington's Pharmaceutical Science, latest edition, Mark Publishing Company, Easton, U.S.A.). The agent may contain a pharmaceutically acceptable carrier and additive together. Examples of such a carrier and a pharmaceutical additive include water, pharmaceutically acceptable organic solvents, collagen, polyvinyl alcohol, polyvinylpyrrolidone, carboxy vinyl polymer, sodium carboxymethylcellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants that are acceptable as pharmaceutical additives. An actual additive is selected alone from the above or an appropriate combination thereof is selected depending on the dosage form of a therapeutic agent of the present invention. Such an additive is not limited to the above. For example, when the therapeutic agent is used in the form of a formulation for injection, it is dissolved in a solvent such as physiological saline, buffer, or a glucose solution, to which an adsorption inhibitor such as Tween80, Tween20, gelatine, or human serum albumin is added, and then the resultant can be used. Alternatively, the therapeutic agent may also be in a freeze-dried dosage form, so that it can be dissolved and reshaped before use. As an excipient for freeze-drying, for example, sugar alcohols such as mannitol and glucose and sugars can be used. A therapeutic agent of the present invention is generally administered via a parenteral route of administration, such as injection (e.g., subcutaneous injection, intravenous injection, intramuscular injection, or intraperitoneal injection), transdermal administration, transmucosal administration, transnasal administration, or transpulmonary administration. Oral administration is also possible.

8. Method for Screening for Substance Binding to Protein of the Present Invention or Partial Peptide Thereof A protein of the present invention is useful in screening for a substance binding thereto. That is, a protein of the present invention is used in a method for screening for a compound binding to the protein of the present invention, which comprises bringing a protein of the present invention into contact with a test sample inferred to contain a compound binding thereto, detecting binding activity between the protein of the present invention and the test sample, and selecting a compound having activity to bind to the protein of the present invention.

A protein of the present invention used in screening may be either a recombinant protein or a protein derived from nature. Such a protein of the present invention may also be a partial peptide described above. Examples of a test sample are not specifically limited and include cell extracts, cell culture supernatants, products of fermentation microorganisms, extracts from marine organisms, plant extracts, purified or roughly-purified proteins, peptides, nonpeptidic compounds, synthetic low-molecular-weight compounds, and natural compounds. A protein of the present invention can be brought into contact with a test sample in the form of, for example, a purified protein, a soluble protein, a protein bound to a carrier, a protein (fusion protein) fused with another protein, a protein being expressed on a cell membrane, or a membrane fraction.

As a method for screening for, for example, a protein (e.g., a ligand) binding to a protein of the present invention, many methods known by persons skilled in the art can be employed. Examples of such a screening method include immunoprecipitation (Harlow, E. and Lane, D.: Antibodies, pp. 511-552, Cold Spring Harbor Laboratory publications, New York (1988)), West-Western blotting method (Skolnik, E. Y. et al., Cell (1991) 65, 83-90), the 2-hybrid system using cells (Fields, S., and Sternglanz, R., Trend. Genet. (1994) 10, 286-292; and Dalton S, and Treisman R., (1992) Characterization of SAP-1, a protein recruited by serum response factor to the c-fos serum response element. Cell, 68, 597-612) ("MATCHMAKER Two-Hybrid System," "Mammalian MATCHMAKER™ Two-Hybrid Assay Kit," "MATCHMAKER™ One-Hybrid System." (all of them are produced by Clontech), and "HYBRIZAP™ Two-Hybrid Vector System" (produced by Stratagene)), a method utilizing affinity chromatography, and a method using a biosensor that utilizes the surface plasmon resonance phenomenon.

Examples of a method for isolating not only a protein but also a compound binding to a protein of the present invention, which are known by persons skilled in the art, include a method that involves causing a synthetic compound, a natural product bank, a random phage peptide display library, or the like to act on an immobilized protein of the present invention, so as to screen for a molecule binding to the protein of the present invention, and a screening method using high throughput based on combinatorial chemistry technology (Wrighton N C; Farrell F X; Chang R; Kashyap A K; Barbone F P; Mulcahy L S; Johnson D L; Barrett R W; Jolliffe L K; Dower W J., Small peptides as potent mimetics of the protein hormone erythropoietin, Science (UNITED STATES) Jul. 26 1996, 273 p458-464; Verdine G L., The combinatorial chemistry of nature, Nature (ENGLAND) Nov. 7 1996, 384 p11-13; and Hogan J C Jr., Directed combinatorial chemistry, Nature (ENGLAND) Nov. 7 1996, 384 p17-17).

A compound that can be isolated by the screening method of the present invention can be a substance for inhibiting binding of a protein of the present invention to a ligand. Hence, the compound can be applied to an anti-carcinoma agent. Specifically, an anti-carcinoma agent can also be produced by mixing a compound isolated by the screening method of the present invention with a pharmacologically acceptable carrier.

Besides, a protein of the present invention is predicted to be a transferase for sugar chains. Thus, it is possible to screen for a protein as a substrate utilizing a lectin that particularly recognizes a sugar chain. "Protein as a substrate" means a protein to which a sugar chain is added by glycosyltransferase activity of the protein encoded by a gene of the present invention.

For example, through the use of a lectin such as PHA-L4 (kidney bean lectin) that recognizes an N-type sugar chain with branches on the position-6 side of β mannose, a protein as a substrate can be identified by analyzing a protein that is expressed at different levels comparing cells expressing a protein of the present invention at high levels and cells expressing the same at low levels. Alternatively, a protein as a substrate can be identified by analyzing changes in molecular weight due to the presence or the absence of sugar transfer by a protein of the present invention. An example of a method for such screening involves analyzing glycoproteins expressed by a culture cell line expressing a gene of the present invention at high levels, such as MCF7 breast carcinoma cell line (ATCC #HTB 22), or DU-145 prostatic adenocarcinoma cell line (ATCC #HTB-81), or PANC-1 pancreatic carcinoma cell line (ATCC #CRL 1469), and by a culture cell line expressing the same at low levels, such as MDA-MB-231 breast carcinoma cell line (ATCC #HTB 26), LNCap.FGC prostatic adenocarcinoma cell line (ATCC #CRL-1740), or BxPC-3 pancreatic carcinoma cell line (ATCC #CRL 1687) by Western blotting or the like using various lectins. Another example of a method for screening for a protein as a substrate involves comparing cells into which a gene of the present invention has been transferred with the original cells, or inhibiting the expression of a protein of the present invention by a cell expressing the gene of the present invention using antisense DNA or siRNA.

Moreover, a sugar chain to be added by glycosyltransferase activity of a protein of the present invention is identified, and it can also be utilized for diagnosis or treatment for carcinoma. For example, a carcinoma-specific sugar chain structure can be screened for by extracting proteins from the above cells expressing the gene of the present invention and then excising sugar chains using an enzyme that specifically cleaves an N-type-binding sugar chain, such as Glycopeptidase F, or by analyzing sugar chains by, for example, HPLC after a chemical reaction such as hydrazinolysis or N acetylation treatment.

The protein as a carcinoma-specific substrate or sugar chain structure screened for in the aforementioned manner can be altered for use in anti-carcinoma agents.

In addition, such an antibody against such a protein as a substrate or a sugar chain structure is expected to show specific reaction to carcinoma, so that anti-carcinoma agents containing such antibodies are useful.

9. Others

An antisense oligonucleotide (DNA) having a nucleotide sequence substantially complementary to that of a DNA encoding a protein of the present invention or a partial polypeptide thereof may be any antisense DNA, as long as it has a nucleotide sequence substantially complementary to the nucleotide sequence of the DNA and has action that can suppress the expression of the DNA. Such a substantially complementary nucleotide sequence is, for example, a nucleotide sequence having preferably approximately 90% or more, more preferably approximately 95% or more, and most preferably 100% homology with the entire or a partial nucleotide sequence complementary to a DNA of the present invention. Furthermore, nucleic acid sequences (modified RNA or DNA) having action similar to that of these antisense DNAs are also included in examples of the antisense DNAs in the present invention. These antisense DNAs can be produced using a known DNA synthesizer or the like.

siRNA (small interfering RNA) is a double-stranded RNA suppressing the expression of a gene within a cell and comprising 21 nucleotides complementary to the gene as reported by Elbashir et al. (Elbashir S M, Harborth J, Lendeckel W, Yalcin A, Weber K, Tuschl T (2001), Nature 411: 494-498). An siRNA having a nucleotide sequence complementary to a mRNA encoding a protein of the present invention or a partial polypeptide thereof may be any siRNA, as long as it has a nucleotide sequence complementary to the nucleotide sequence of the mRNA and has action capable of suppressing the expression of the mRNA. siRNA has two nucleotides, UU or TT, overhanging at the 3' terminus, and is a double-stranded RNA wherein a sense RNA comprising 19 nucleotides complementary to a gene of the present invention hybridizes to an antisense RNA. For example, such an siRNA can be prepared according to the manuals of a kit such as Silencer™ siRNA Construction Kit (#1620), Silencer™ siRNA Labeling Kit-Cy3 (#1632), Silencer siRNA Labeling Kit-FAM (#1634), or Silencer™ Transfection Kit (#1630) of Ambion. Alternatively, such an siRNA can also be prepared by chemical synthesis. The chain length of an siRNA is particularly preferably 21 nucleotides or more or 25 nucleotides or more. Specifically, an siRNA may be of any length, as long as it has action capable of suppressing the expression of the mRNA. Furthermore, it has been reported that an siRNA labeled with Cy3, FAM, or the like has suppressive action equivalent to that of an siRNA alone. Thus, an siRNA used herein may be an siRNA modified with one of these labels.

Furthermore, for stable expression of an siRNA, an siRNA may be expressed by an expression vector (Brummelkamp, T R et al., (2002) Science 296: 550-553; Paddison, P J et al., (2002) Genes & Dev. 16: 948-958; Paul, C P et al., (2002) Nature Biotechnol. 20: 505-508; Sui, G et al., (2002). Proc. Natl. Acad. Sci. U.S.A., 99(6): 5515-5520; Yu, J-Y et al., (2002) Proc. Natl. Acad. Sci. U.S.A., 99(9): 6047-6052; Miyagishi, M, and Taira, K (2002). Nature Biotechnol. 20: 497-500; and Lee, N S et al., (2002) Nature Biotechnol. 20: 500-505). For example, by the utilization of a polymerase III H1 RNA or an U6 promoter as a promoter to be recognized by an RNA polymerase III, a sequence with a length of 20 nucleotides or more of a gene of the present invention is inserted between the promoter and a transcription termination signal sequence so that an inverted repeat is formed and the gene is then expressed. A sequence to be inserted herein may be any sequence, as long as it has a nucleotide sequence complementary to the nucleotide sequence of the mRNA and has action capable of suppressing the expression of the mRNA.

For a carcinoma patient experiencing abnormal expression of a gene of the present invention, the activity of the protein of the present invention in the patient can be inhibited by suppressing gene expression by these methods. In addition to a method that involves direct introduction of an antisense DNA and an siRNA into a patient body, there is an example of such a method that involves carrying out gene therapy using an appropriate vector as a vehicle, such as a retrovirus vector, an adenovirus vector, or an adenovirus-associated virus vector. Furthermore, such a DNA and siRNA can also be administered together with an adjuvant for intake acceleration by a gene gun or via a catheter such as a hydrogel catheter.

Moreover, a single nucleotide mutation in a DNA or a gene of the present invention, which differs depending on individuals; that is, cSNPs can be found by carrying out PCR using synthetic DNA primers (prepared based on the nucleotide sequence of a DNA or a gene of the present invention or a partial nucleotide sequence thereof) and chromosomal DNA extracted from human blood or tissue and then determining the nucleotide sequence of the product. Accordingly, individual constitution and the like are predicted, so that development of a medicine appropriate for each individual and the like is enabled.

Furthermore, through the use of cross hybridization, causative genes of human diseases can be searched for and identified by isolating orthologous (homolog or counterpart) genes against DNAs or genes of the present invention in a model organism such as a mouse, and then producing a human disease model animal by, for example, knocking out these genes.

In addition, in this specification and tables, when nucleotides or amino acids are denoted with abbreviations, such abbreviations are based on the IUPAC-IUB Commission on Biochemical Nomenclature or abbreviations commonly used in the art. When optical isomers can be present for amino acids, they are L-isomers, unless specified.

This specification includes part or all of the contents as disclosed in the specification and/or drawings of Japanese Patent Application No. 2002-338549, which is a priority document of the present application.

BRIEF DESCRIPTION OF THE DRAWINGS

Figure 1:
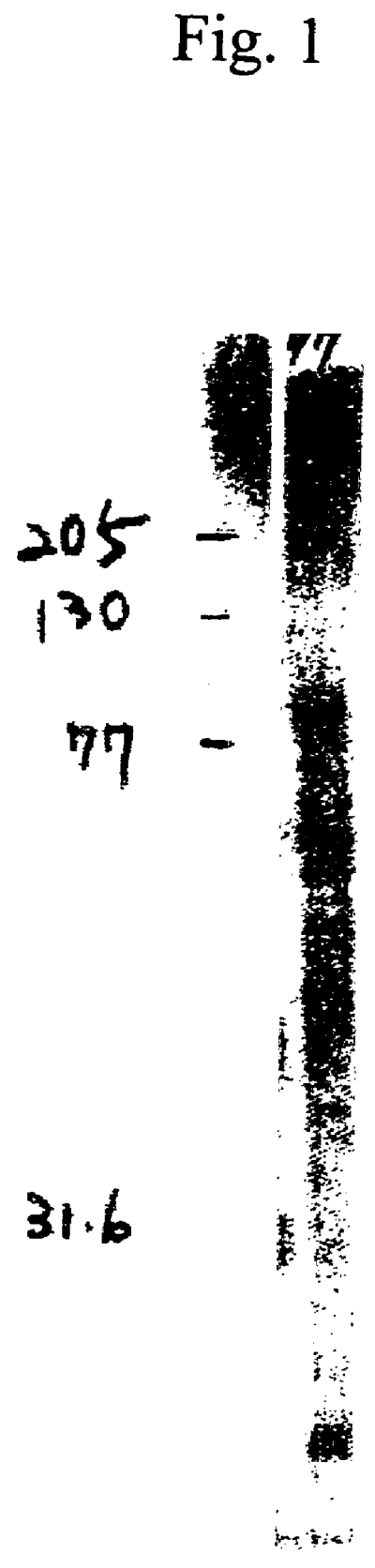

FIG. 1 shows electrophoresis of FJ04470 expressed by in vitro transcription.

FIG. 2 shows alignment of the amino acid sequences of GnT-V and FJ04470.

BEST MODE FOR CARRYING OUT THE INVENTION

Figure 3:
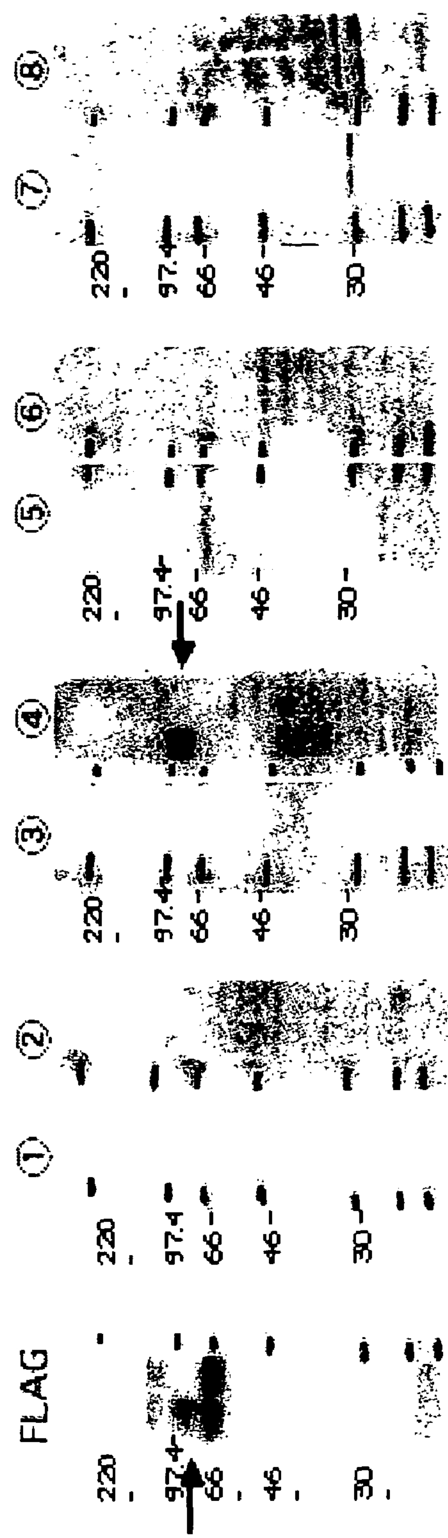
FIG. 3 is a photograph showing the results of Western blotting of FJ04470.

The present invention will be further specifically described as follows by reference to examples, but it is not limited thereto. In addition, various genetic manipulations in the examples are conducted according to the method described in the above Current Protocols in Molecular Biology (edited by Frederick M. Ausubel et al., 1987).

EXAMPLE 1

Obtainment of DNA of the Present Invention (1) Construction of cDNA Libraries Derived from Human Adult Whole Brain, Human Tonsil, Human Hippocampus, and Human Fetal Whole Brain Double-stranded cDNAs were synthesized with a SuperScriptII reverse transcriptase kit (Invitrogen) using an oligonucleotide (GACTAGTTCTAGATCGCGAGCGGCCGCCC$(T)_{15}$) (SEQ ID NO:5)(Invitrogen) having an Not I site as a primer and mRNAs (Clontech) derived from human adult whole brain, human tonsil, human hippocampus, and human fetal whole brain as templates. Adaptors (Invitrogen) having Sal I sites were ligated to cDNAs. Subsequently, the resultants were digested with Not I, and then DNA fragments of 3 kb or more were purified by low melting agarose electrophoresis with 1% concentration.

Purified cDNA fragments were ligated to pBluescript IISK+plasmids that had been digested with Sal I-Not I restriction enzymes. The recombinant plasmids were introduced into *Escherichia coli* ElectroMax DH10B strain (Invitrogen) by an electroporation method.

(2) Screening 1

Subsequently, clones were randomly picked up from the thus constructed cDNA libraries, and then spotted onto membranes. Each 3' terminus of mixtures of oligo DNAs (21 nucleotides each, produced based on the nucleotide sequences of approximately 1300 clones, where the full-length sequences thereof had already been analyzed by the present inventors) was DIG-labeled with terminal transferase. Dot hybridization (Current Protocols in Molecular Biology (edited by Frederick M. Ausubel et al., 1987)) was carried out using the same as probes, so that duplicated clones (clones that had appeared repeatedly) were removed.

Next, in vitro transcription and translation (Promega, TNT T7 ™ Quick Coupled Transcription/Translation System cat-.no.L1107) were carried out, and then clones for which products of 50 kDa or more had been confirmed were selected.

Next, the terminal nucleotide sequences of the selected clones were determined. With the thus obtained sequences as queries, the nr database (All GenBank+EMBL+DDBJ+PDB sequences (but no EST, STS, GSS, or phase 0, 1, or 2 HTGS sequences)) was homology-searched using the BLASTN 2.2.1 homology search program (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs," Nucleic Acids Res. 25: 3389-3402). For sequencing, a DNA sequencer (ABI PRISM™377) produced by PE Applied Biosystem and a reaction kit produced by the same were used. Most sequences were determined by a dye terminator method using shotgun clones. Some nucleotide sequences were determined by synthesizing oligonucleotides based on the determined nucleotide sequences, and then carrying out a primer walking method.

Thus, novel DNAs or genes were screened for. As a result, a clone FJ04470 was discovered from a cDNA produced from human fetal brain-derived polyA+RNA.

(3) Expression of Protein Encoded by Gene of the Present Invention

By the use of an in vitro transcription and translation system (Promega, TNT T7 ™ Quick Coupled Transcription/Translation System cat. no. L1107), a gene product from the cDNA clone FJ04470 was expressed.

The product, in which $^{35}$S-labeled methionine had been incorporated was subjected to 12.5% SDS-PAGE electrophoresis. Gel was dried, autoradiography was carried out using a BAS2000 (FUJIFILM) system, and then the gene product of the clone FJ04470 was detected. The size of the FJ04470 product was 90 kDa as measured using a size marker (Cat. 161-0324) of KALEIDOSCOPE™ Prestained Standards of Bio-Rad.

The protein encoded by FJ04470 comprised 793 amino acid residues when counted from the first methionine and the molecular weight thereof was inferred to be approximately 89.4 kDa, which agreed well with the experimental result.

EXAMPLE 2

Homology of DNA of the Present Invention (4) Homology Search of DNA of the Present Invention Next, by the use of BLASTN 2.1.3, BLASTP 2.1.3 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs," Nucleic Acids Res. 25: 3389-3402), NCBI nt (non-redundant nucleotide database), nr (non-redundant protein database), and patent sequence databases (geneseqnt and geneseqaa) were homology-searched.

As a result, it was revealed that the FJ04470 gene showed homology with the genes shown in Table 1. The FJ04470 gene is a gene comprising 4491 bp encoding the protein consisting of 793 amino acids, wherein a sequence ranging from the $575^{th}$ to the $2950^{th}$ nucleic acids of the nucleic acid sequence encodes amino acids.

When compared with the gb human gene: T50606 (hypothetical protein DKFZp761J107.1) that had been shown to have high homology with the FJ04470 gene, the N-terminus of FJ04470 was longer than that of the gb gene by 254 amino acids. Thus it was considered that the FJ04470 gene encodes a full-length gene of the same gene. gb: T50606 was an amino acid sequence that had been predicted by computer and was a partial sequence that lacks hydrophobic regions (thought to be transmembrane regions existing on the N-terminus) and 4 sugar chain-binding sites. Thus it cannot be said to be a functional molecule.

gb: AAC52925, which had been shown next to have homology by the use of the databases, is a transferase for sugar chains, referred to as alpha-1,3(6)-mannosylglycoprotein beta-1,6-N-acetyl-glucosaminyltransferase, and it is expressed in CHO cells. The FJ04470 gene had 44% homology with 45.5% (region) of the enzyme, suggesting that the gene is one of glycosyltransferases. gb: NP_002401.1, which had been shown next to have homology, is a human ortholog of gb:AAC52925. Thus, gb: NP_002401.1 and FJ04470 protein were compared for their amino acid sequences in detail. GAP of GCG Wisconsin Package (Accelrys) was used. Among 21 cysteine residues, 19 cysteine residues following the $157^{th}$ cysteine residue of the FJ04470 protein were found to be almost analogous in arrangement with gb: AAC52925, excluding one of 20 cysteine residues.

Thus, it can be inferred that structures obtained as a result of protein folding by disulfide bonding can be quite analogous to each other.

TABLE 1

FJ04470 protein homology

| Clone Homologous region | Homologous gene | Homologous gene Homologous region | Score | E-value | Homology | Homologous region ratio |
|---|---|---|---|---|---|---|
| 255–792 | T50606 hypothetical protein DKFZp761J107.1 (*Homo sapiens*) | 1–538 | 1130 | 0.0 | 537/538 (99%) | 537/538 (99%) |
| 55–792 | AAC52925 beta-1,6-N-acetylglucosaminyltransferase (*Cricetulus griseus*)*1 | 32–740 | 620 | e−176 | 337/758 (44%) | 337/740 (45.5%) |
| 55–792 | NP_002401.1 alpha-mannoside beta-1,6-N-acetylglucosaminyltransferase (*Homo sapiens*)*2 | 32–741 | 615 | e−174 | 332/759 (43%) | 332/741 (44.8%) |

Table 1 shows information concerning the homologous genes. In addition, the meaning of each item in Table 1 is as follows.

Homologous region and Clone: the starting and ending points of a homologous region of a clone Homologous region and Homologous gene: the starting and ending points of a homologous region of a homologous gene Score: The higher the score, the higher the reliability E-value: The closer the E-value to 0, the higher the reliability Homology: The ratio of identity between amino acid residues in homologous regions The homologous region ratio: The ratio of a homologous region to the entire region in a homologous gene The Pfam database (http://www.sanger.ac.uk/Software/Pfam/) was motif-searched concerning peptide sequences by HMMER 2.1.1 (Bioinformatics 14: 755-763, (1998)), but no hit motifs were present.

As a result of searches by PSORT II (http://psort.nib-b.ac.jp/), a program for inferring hydrophobic regions and intracellular localization, it was predicted that a region from the 25$^{th}$ amino acids to the 41$^{st}$ amino acids is a transmembrane region and that it is a type II membrane protein that is same as other glycosyltransferases wherein the N-terminus exists within the cytoplasm. Further analyses using PEPTIDESTRUCTURE of GCG Wisconsin Package (Accelrys) revealed the presence of N-type sugar-chain binding sites at 8 positions (the 93rd, the 127th, the 215th, the 236th, the 447th, the 600th, the 666th, and the 675th amino acid residues). Thus, it was considered that the FJ04470 protein is a glycoprotein.

(2) Comparison with Genome Sequence gb:AC016168.18 (Homo sapiens chromosome 17, clone RP11-87G24, complete sequence, length=193537) as a result of homology searches by BLASTN 2.1.3 was compared with the FJ04470 gene. As a result, the FJ04470 gene was found to extend from the 147788th to the 65867th positions of the genome sequence of gb:AC016168.18. The FJ04470 gene has 19 separate exons, where coding regions were separately present within a range from the 2$^{nd}$ exon to the 18$^{th}$ exon. The result of comparing the FJ04470 gene with the genome sequence is shown in Table 2.

Furthermore, the FJ04470 protein and gb:AC016168.18 were compared for their nucleic acid sequences using the Genewise program of Wise2-1-20c (http://www.sanger-.ac.uk/Software/Wise2), thereby specifying junction sites of each exon-intron.

gb:XM_085533 mRNA (Homo sapiens hypothetical protein FLJ25132 (FLJ25132)) has been reported as a gene predicted by computer. However, it agreed 99% (1132/1133) with a nucleic acid sequence ranging from the 362$^{nd}$ to the 1493$^{rd}$ nucleic acids of the FJ04470 gene. This contains a sequence extending only to the 4$^{th}$ exon (from the 1$^{st}$ to the 3$^{rd}$ coding exons). The presence of a large intron comprising 20255 nucleotides between the 4$^{th}$ and the 5$^{th}$ exons was revealed by Genewise analysis. Thus, it was considered that this long intron was unpredictable by the NCBI computer program. Specifically, FJ04470 is a gene unpredictable by computer because the exon structure of FJ04470 cDNA contains such a large intron.

Table 2 Comparison between FJ04470 cDNA sequence and genome sequence

The FJ04470 cDNA sequence and the genome sequence were analyzed concerning exon and intron boundaries by Genewise, and the thus obtained exon sizes and intron sizes were listed in Table 2.

Numbers for the cDNA and the corresponding numbers for the genome sequence of gb:AC016168.18 are aligned on the left and the right, respectively.

TABLE 2

| FJ04470 | AC016168.18 | Exon Size | Intron Size |
|---|---|---|---|
| 1 | 147788 | | |
| 96 | 147693 | 95 | |
| 160 | 147629 | | 64 |
| 643 | 147146 | 483 | |
| 642 | 143394 | | 3752 |
| 755 | 143281 | 113 | |
| 754 | 134095 | | 9186 |
| 904 | 133945 | 150 | |
| 902 | 113691 | | 20254 |
| 1019 | 113574 | 117 | |
| 1019 | 112942 | | 632 |
| 1093 | 112868 | 74 | |
| 1092 | 111994 | | 874 |
| 1265 | 111821 | 173 | |
| 1260 | 111080 | | 741 |
| 1429 | 110911 | 169 | |
| 1427 | 110229 | | 682 |
| 1599 | 110057 | 172 | |
| 1598 | 91280 | | 18777 |
| 1734 | 91144 | 136 | |
| 1731 | 89648 | | 1496 |
| 1865 | 89514 | 134 | |
| 1866 | 83599 | | 5915 |
| 1996 | 83469 | 130 | |

TABLE 2-continued

| FJ04470 | AC016168.18 | Exon Size | Intron Size |
|---|---|---|---|
| 1998 | 78261 | | 5208 |
| 2158 | 78101 | 160 | |
| 2159 | 75842 | | 2259 |
| 2308 | 75693 | 149 | |
| 2304 | 75514 | | 179 |
| 2424 | 75394 | 120 | |
| 2420 | 69871 | | 5523 |
| 2498 | 69793 | 78 | |
| 2495 | 68417 | | 1376 |
| 2755 | 68157 | 260 | |
| 2755 | 67604 | | 553 |
| 3574 | 66785 | 819 | |
| 3628 | 66731 | | 54 |
| 4491 | 65867 | 863 | |

(3) Gene Expression Information in Public Database

The FJ04470 gene belongs to Unigene cluster of Hs.144531 based on homology searches of the Unigene database. There are 33 EST clones belonging to Hs.144531. These ESTs thereof are derived from brain, liver, pancreas (exocrine), germ cells (pooled), breast, cervix, lung, spleen, eyes, pancreas, dorsal root ganglia, or ovary. It was observed that cDNAs tended to be derived from brain (15/33). With the expression information obtained from public databases, it is unknown whether or not the gene is expressed specifically in carcinoma.

EXAMPLE 3

Transcriptional Analysis of DNA of the Present Invention (1) Analysis of Transcript by Real-Time PCR The amount of the transcript of the gene of the present invention was analyzed by the ABI PRISM™ (registered trademark) 7700 Sequence Detection System (ABI) using cDNAs of various tissues. For analysis of expression levels of GAPDH gene, a Pre-Developed TAQMAN™ PCR Assay Kit (ABI, #4310884E) was used. The composition for the PCR reaction was as follows. 5 μl of MTC Panel cDNA (Clontech) was added to Master Mix (a mixture of 1.25 μl of 20× Control Mix (GAPDH), 6.25 μl of DEPC-treated water (Ambion, #9920), and 12.5 μl of TAQMAN™ Universal PCR Master Mix (ABI, #4304437)) to 25 μl. Gene amplification was carried out for 40 cycles, each cycle consisting of 50° C. for 2 minutes, 95° C. for 10 minutes, and 95° C. for 15 seconds −60° C. for 1 minute) using an ABI PRISM™ (registered trademark) 7700 Sequence Detection System of ABI on a MicroAmp Optical 96-Well Reaction Plate (ABI, #N801-0560). As MTC Panel cDNAs, Human MTC™ Panel I (K1420-1), Human MTC™ Panel II (K1421-1), and Human Tumor MTC™ Panel I (K1422-1) of Clontech were used. Total RNA was collected by ISOGEN™ (Wako Pure Chemical Industries) from the cultured carcinoma cells and then the genomic DNA was digested using amplification grade Dnase I (Invitrogen). The method was carried out according to the manual recommended by Invitrogen. The total RNA treated with DNase I was reverse-transcribed into a cDNA using Invitrogen superscript II reverse transcriptase.

Regarding the expression levels of the gene of the present invention, primer sequences that were optimal for RT-PCR were searched for using PrimerExpress 1.5 of ABI. When the sequence of the FJ04470 gene was compared with the genome sequence, the sequence matched the sequence of AC016168.18. As a result of analyzing intron and exon structures, the presence of an intron comprising approximately 2260 nucleotides were inferred in the vicinity of the nucleotide number of 2158 of FJ04470. Thus, primer positions were determined so that they sandwiched the region. When primer 4470-2043 (5'-AGATCCATGGCACCGTGTACTAC-3') and primer 4470-2230 (5'-GAAGATGCAACCATTGGCG-3') are used, 188 nucleotides will be amplified in the case of cDNA and approximately 2450 nucleotides will be amplified in the case of the genome. 0.5 μl of 10 μM primer 4470-2043, 0.5 μl of 10 μM primer 4470-2230, 6.5 μl of DEPC-treated water, and 12.5 μl of SYBR Green PCR Master Mix (ABI, #4309155) were mixed to 20 μl. 1 μl of MTC Panel cDNA (Clontech) and 4 μl of DEPC-treated water (treated water) were added to the mixed solution to 25 μl. Gene amplification was carried out for 40 cycles, each cycle consisting of 50° C. for 2 minutes, 95° C. for 10 minutes, and 95° C. for 20 seconds-60° C. for 1 minute) using an ABI PRISM™ (registered trademark) 7700 Sequence Detection System of ABI on the MicroAmp Optical 96-Well Reaction Plate of ABI (ABI, #N801-0560). A standard curve was created using a plasmid into which a GAPDH amplicon (the expression level of the GAPDH gene was used as an internal control) had been cloned. Based on the curve, the number of copies existing in the reaction solution was calculated. Table 3 below shows the results of comparing the expression levels in different tissues using relative values obtained by dividing each expression level of the gene of the present invention by each expression level of the GAPDH gene.

In Table 3, tissue names are on the left side and each numerical value on the right side shows the expression level of the FJ04470 gene normalized using the expression level of GAPDH gene in each tissue. The value in the liver is considered to be 1 and the expression levels in other tissues are shown as relative values.

As understood from Table 3, high expression levels were observed in lung carcinoma and prostatic adenocarcinoma. In the case of normal tissues, high expression levels were observed in the brain and the testis; however, the expression levels in other tissues were not so high.

Table 3 Analysis of Transcript by Real-Time PCR (1)

To compare the expression levels of FJ04470, relative values obtained by dividing each expression level of FJ04470 by each expression level of GAPDH (measured as the internal control) were compared. The relative expression level in the liver is considered to be 1, and the expression levels in various tissues were compared.

TABLE 3

| Sample | |
|---|---|
| Heart | 0.56 |
| Brain | 59.97 |
| Placenta | 0.36 |
| Lung | 1.80 |
| Liver | 1.00 |
| Skeletal muscle | 0.00 |
| Kidney | 1.37 |
| Pancreas | 1.25 |
| Spleen | 2.89 |
| Thymus gland | 1.15 |
| Prostate | 1.77 |
| Testis | 13.87 |
| Ovary | 3.85 |
| Small intestine | 2.87 |
| Large intestine | 0.81 |
| PBL | 0.00 |
| Breast carcinoma GI-101 | 0.90 |
| Lung carcinoma LX-1 | 4.74 |

TABLE 3-continued

| Sample | |
|---|---|
| Colon adenocarcinoma CX-1 | 2.02 |
| Lung carcinoma GI-117 | 16.86 |
| Prostatic adenocarcinoma PC3 | 89.28 |
| Colon adenocarcinoma GI-112 | 0.29 |
| Ovarian carcinoma GI-102 | 0.72 |
| Pancreatic adenocarcinoma GI-103 | 1.62 |

Furthermore, to compare expression levels in various carcinoma cell lines, the expression of the FJ04470 gene was analyzed using cDNAs of 31 types of carcinoma cells and 4 types of normal cells.

As a result, high expression was observed in lung carcinoma, breast carcinoma, prostatic adenocarcinoma, and pancreatic carcinoma. Accordingly, the gene of the present invention is a gene the expression of which was elevated in lung carcinoma, breast carcinoma, prostatic adenocarcinoma, and pancreatic carcinoma. Thus, it was considered that the protein encoded by the gene will also be expressed at high levels in these tissues.

Only the SW620 cells were observed to express the gene at a high level among the colon carcinoma cell line items. The SW620 cells were obtained from a site to which colon carcinoma had metastasized to a lymph node, suggesting association of the gene of the present invention with metastasis.

Table 4 Analysis of Transcript by Real-Time PCR (2)

To compare the expression levels of FJ04470, relative values obtained by dividing each expression level of FJ04470 by the expression level of GAPDH (measured as the internal control) were compared. The relative expression level in mammary epithelial cells was considered to be 1, and the expression levels in various carcinoma cells were compared.

TABLE 4

| Sample Name | Cell Type | 4470/GAPDH HMEC = 1 |
|---|---|---|
| A549 | Lung carcinoma | 5.3 |
| NCI-H460 | Lung carcinoma | 2.0 |
| NCI-H23 | Lung carcinoma | 4.1 |
| NCI-H522 | Lung carcinoma | 9.1 |
| HT-29 | Colon carcinoma | 0.0 |
| LS 174T | Colon carcinoma | 0.3 |
| COLO 205 | Colon carcinoma | 0.0 |
| LoVo | Colon carcinoma | 0.0 |
| SW620 | Colon carcinoma | 12.9 |
| MCF7 | Breast carcinoma | 36.3 |
| MDA-MB-231 | Breast carcinoma | 5.8 |
| ZR-75-1 | Breast carcinoma | 6.4 |
| BT-474 | Breast carcinoma | 4.7 |
| DU-145 | Prostatic adenocarcinoma | 19.4 |
| PC-3 | Prostatic adenocarcinoma | 7.7 |
| LNCap.FGC | Prostatic adenocarcinoma | 0.0 |
| 22Rv1 | Prostatic adenocarcinoma | 2.7 |
| BALL-1 | Leukemia | 0.0 |
| P39/TSU | Leukemia | 0.0 |
| KU812 | Leukemia | 1.4 |
| CCRF-CEM | Leukemia | 5.4 |
| JOK-1 | Leukemia | 1.5 |
| Daudi | Lymphoma | 0.4 |
| EB-3 | Lymphoma | 0.6 |
| Ramos | Lymphoma | 0.2 |
| P3HR-1 | Lymphoma | 1.5 |
| BxPC-3 | Pancreatic carcinoma | 0.0 |
| Capan-1 | Pancreatic carcinoma | 1.8 |
| MIA PaCa-2 | Pancreatic carcinoma | 7.6 |
| PANC-1 | Pancreatic carcinoma | 22.9 |
| AsPC-1 | Pancreatic carcinoma | 2.9 |
| HAEC | Aortic endothelium | 0.0 |

TABLE 4-continued

| Sample Name | Cell Type | 4470/GAPDH HMEC = 1 |
|---|---|---|
| HMEC | Mammary epithelium | 1.0 |
| PrEC | Prostate epithelium | 0.8 |
| SAEC | Small airway epithelium | 0.7 |

EXAMPLE 4

Preparation of Polyclonal Antibody 2 different regions with high antigenicity were selected by comparison with GnT-V sequence (having the highest homology), thereby preparing polyclonal antibodies.

FIG. 2 shows the alignment of GnT-V and FJ04470 amino acid sequences. Numerals shown in FIG. 2 denote the amino acid numbers of FJ04470 and each amino acid is denoted with a single letter. The consensus sequence resulting from comparison with GnT-V is shown in every third item in the left column. Sequences used for preparation of peptide antibodies are two underlined portions (a portion of 11 amino acids and a portion of 15 amino acids). The other underlined portions denote sites to which addition of an N-type sugar chain is inferred.

Selected peptide sequences (AG and RA) are AG: CAGSNTKYRRL (SEQ ID NO: 3) and RA: CRAPDPALPEAHAPQ (SEQ ID NO: 4). Peptide synthesis and preparation of rabbit polyclonal antibodies were assigned to Promega Corporation. After a 11-mer peptide (AG) and a 15-mer peptide (RA), each of which had purity of 80% or more purity, were synthesized, KLH was conjugated thereto, and then two rabbits were immunized with each peptide. Female rabbits (Japanese White) with body weights between 2.5 kg and 3.0 kg each were used. As adjuvants, FCA was used in the initial immunization and IFCA was used in 5 instances of booster immunization, where 0.5 mg of IFCA was used for each immunization.

An expression vector prepared by cloning FJ04470-FLAG into pcDNA3.1 (Invitrogen) was introduced into COS cells. 48 hours later, the cells lysed in an SDS-PAGE sample buffer were separated by SDS-PAGE.

After completion of SDS-PAGE, gel was immersed in a transfer buffer (1M Tris (pH7.5) 48 ml, 2.928 g of glycine, and 200 ml of MtOH/L), followed by 60 minutes of blotting at 20 V using a PVDF membrane (Immobilon-P, Nihon Millipore K. K., IPVH 304 FO) using BioRad Trans-Blot SD. The membrane to which proteins were transferred was subjected to blocking with 2% skim milk (Snow Brand Milk Products)/T-TBS at 4° C. overnight. Subsequently, the resultant was allowed to react with a rabbit anti-peptide antiserum diluted 1000 fold at room temperature for 1 hour. The resultant was washed 3 times with T-TBS (10 minutes per washing) while shaking, followed by reaction with a secondary antibody. Anti-rabbit Ig (HRP linked F(ab')2 fragment (from donky)) (Amersham) was diluted 5000 fold with 2% skim milk (Snow Brand Milk Products)/T-TBS, and then the resultant was allowed to react at room temperature for 1 hour. The resultant was washed 4 times with T-TBS (10 minutes per washing) while shaking, and then bands reacting with peptide antibodies were detected using an ECL detection kit (Amersham). As a result, a band of FJ04470 of approximately 90 KDa, the same size as that of a band detected with an anti-FLAG antibody, was detected in an RA2 rabbit. Since the band was detected as a broad band, it was considered that the FJ04470 had been subjected to sugar chain modification.

FIG. 3 shows the results of Western blotting. FIG. 3 shows the results of separating by SDS-PAGE FJ04470-FLAG having an FLAG-tagged C-terminus (transiently expressed in COS7 cells) and cell lysates of the COS7 cells, followed by detection using the rabbit anti-peptide antiserum. The result denoted with FLAG is a control detected using an anti-FLAG antibody. Band positions indicated with arrows are the band positions of the FJ04470-FLAG protein. It was clearly observed that a specific band could be detected in an RA2 030225 sample.

All publications, patents, and patent applications cited herein are incorporated herein by reference in their entirety.

INDUSTRIAL APPLICABILITY

Based on the above findings, the gene of the present invention is a novel gene, the expression of which is elevated in association with carcinoma, and thus can be used for carcinoma diagnosis. In particular, since the gene is expressed at high levels in lung carcinoma, breast carcinoma, prostatic adenocarcinoma, pancreatic carcinoma, and the like, the gene is useful in diagnosis of these types of carcinoma. Examples of a method of diagnosis include DNA diagnosis and a method that involves immunohistostaining using antibodies.

Furthermore, the gene is also useful in diagnosis of carcinoma that has metastasized.

Moreover, carcinoma may be suppressed by, for example, inhibiting functions of the protein as a glycosyltransferase, which is encoded by the gene. Examples of a method for inhibiting such functions include a method for inhibiting functions using antibodies and a method for inhibiting functions using low-molecular-weight substances. In particular, such an antibody or a low-molecular-weight substance is useful as a therapeutic drug or a prophylactic drug for carcinoma such as lung carcinoma, breast carcinoma, prostatic adenocarcinoma, or pancreatic carcinoma.

Furthermore, the gene can also be utilized as a means for screening for a substrate protein as a glycosyltransferase for a sugar chain or for a sugar chain to be transferred to a substrate protein. For example, a protein or a sugar chain to which a sugar is added by the protein of the present invention in association with carcinoma is useful as a target molecule of a therapeutic drug or a prophylactic drug for carcinoma. The use of antibodies against the same or sugar analogues can lead to development of a therapeutic drug or a prophylactic drug for carcinoma. Thus, the gene of the present invention is also useful for such screening.

The invention claimed is:

1. An isolated DNA comprising a nucleotide sequence encoding a polypeptide, comprising the amino acid sequence of SEQ ID NO: 2.

2. An isolated DNA comprising the nucleotide sequence of SEQ ID NO: 1 and containing the nucleotide sequence that encodes the amino acid sequence of SEQ ID NO: 2.

3. An expression vector, comprising a DNA comprising a nucleotide sequence encoding a polypeptide, comprising the amino acid sequence of SEQ ID NO: 2; or a DNA, comprising the nucleotide sequence SEQ ID NO: 1 and containing the nucleotide sequence that encodes the amino acid sequence of SEQ ID NO: 2.

4. A transformant, comprising the vector of claim 3.

5. A method for producing a protein comprising expressing a protein comprising SEQ ID No. 2 by culturing the transformant according to claim 4.

* * * * *

SEQUENCE LISTING

```
<160> NUMBER OF SEQ ID NOS: 7

<210> SEQ ID NO 1
<211> LENGTH: 8982
<212> TYPE: DNA
<213> ORGANISM: Homo sapiens

<400> SEQUENCE: 1

gcggggccgg acgccggaca ccagagcgcg ggcggcggag ccagcgggcg agagagcgcg     60

cggcgggcgc gggttgccct cgtcgagagc catgggcgcg gcgcggcgcg gggctgagga    120

tcggcgcggc ccggaggcgc tggggaccgg ggcgcgggcc cggggccgcc tttagccggc    180

accgagggcg cggggccggg gatgagggcg cccgccgcgg ggagcccgtc tgcgcgccgc    240

ggcaccttcc cgcccagcga gcgagcccga gcaggcagac gcgcggccgg cggtctgggg    300

gcgcgccgcc tcccggtccc caaaatgtga agcggggagg gcggagacgc agagacggcc    360

cggccgggcg ccctcgccgc cctccggcag ccgcgccgct ccctccgctg cacgcccagg    420

cctgagcagc gaggccaccg ggccgcgcgc tcccagcttc gctcggacgc ggcttcggcc    480

cgcagagggt tcgtggcccg gacgcggcga gagctgggcc caggacggtg cgtccggcct    540

cgcccgcggc tgctcgcacc aacaagtttg aacaatgatc accgtcaacc ccgatgggaa    600

gataatggtc agaagatgcc tggtcaccct gagacccttt cggctttttg tcctgggcat    660

cggcttcttc actctctgct tcctgatgac gtctctggga ggccagttct cggcccggcg    720

cctgggggac tcgccattca ccatccgcac agaagtgatg gggggccccg agtcccgcgg    780

cgtcctgcgc aagatgagcg acctgctgga gctgatggtg aagcgcatgg acgcactggc    840

caggctggag aacagcagtg agctgcaccg ggccggcggc gacctgcact ttcccgcaga    900

caggatgccc cctggggccg gcctcatgga gcggatccag gctattgccc agaacgtctc    960

cgacatcgct gtgaaggtgg accagatcct gcgccacagt ctgctcctgc acagcaaggt   1020

gtcagaaggc cggcgggacc agtgtgaggc acccagtgac cccaagttcc ctgactgctc   1080
```

-continued

```
agggaaggtg gagtggatgc gtgcccgctg gacctctgac ccctgctacg ccttctttgg   1140
ggtggacggc accgagtgct ccttcctcat ctacctcagt gaggtcgagt ggttctgccc   1200
cccgctgccc tggaggaacc agacggctgc ccagagggca cccaagcccc tccccaaagt   1260
ccaggcagtt ttccgaagca acctgtccca ccttctggac ctgatgggca gcgggaagga   1320
gtccctgatc ttcatgaaga agcggaccaa gaggctcaca gcccagtggg cgctggctgc   1380
ccagcgcctg gcacagaagc tgggggccac ccagagggac cagaagcaga tcctggtcca   1440
catcggcttc ctgacggagg agtccgggga cgtgttcagc cctcgggtcc tgaagggcgg   1500
gcccctaggg gagatggtgc agtgggcgga cattctgact gcactctatg tcctgggcca   1560
tggcctgcgg gtcacagtct ccctgaagga gctgcagagt aacttagggg taccgccagg   1620
ccggggaagc tgcccgctca ccatgcccct gcccttcgac ctcatctaca ccgactacca   1680
cggcctgcag cagatgaagc ggcacatggg actctccttc aagaagtacc ggtgccgaat   1740
cagggtcatc gacaccttcg ggacggaacc tgcgtacaac cacgaggagt acgccacgct   1800
gcacggctac cggaccaact ggggctactg gaacctcaac cccaagcagt tcatgaccat   1860
gtttcctcat acccccgaca actccttcat gggcttcgtg tccgaggagc tcaacgagac   1920
ggagaagcgg ctcatcaaag gcggcaaggc cagcaacatg gccgtggtgt acggcaagga   1980
ggcgagcatc tggaagctcc aggggaagga gaagttcctg ggcatcctga acaaatacat   2040
ggagatccat ggcaccgtgt actacgagag ccagcggccc cccgaggtgc cagcctttgt   2100
gaagaaccac ggcctcttac cgcagcctga gtttcagcag ctgctgcgca aggccaaact   2160
cttcatcggg tttggcttcc cctacgaggg ccccgccccc ctggaggcca tcgccaatgg   2220
ttgcatcttc ctgcagtccc gcttcagccc gccccacagc tccctcaacc acgagttctt   2280
ccgaggcaag cccacctcca gagaggtgtt ctcccagcat ccctacgcgg agaacttcat   2340
cggcaagccc cacgtgtgga cagtcgacta caacaactca gaggagtttg aagcagccat   2400
caaggccatt atgagaactc aggtagaccc ctacctaccc tacgagtaca cctgcgaggg   2460
gatgctggag cggatccacg cctacatcca gcaccaggac ttctgcagag ctccagaccc   2520
tgccctacca gaggcccacg ccccgcagag cccctttgtc ctggccccca atgccaccca   2580
cctcgagtgg gctcggaaca ccagcttggc tcctggggcc tggcccccccg cgcacgccct   2640
gcgggcctgg ctggccgtgc ctgggagggc ctgcaccgac acctgcctgg accacgggct   2700
aatctgtgag ccctccttct tccccttcct gaacagccag gacgccttcc tcaagctgca   2760
ggtgccctgt gacagcaccg agtcggagat gaaccacctg tacccggcgt tcgcccagcc   2820
tggccaggag tgctacctgc agaaggagcc tctgctcttc agctgcgccg gctccaacac   2880
caagtaccgc cggctctgcc cctgccgcga cttccgcaag ggccaggtgg ccttgggcca   2940
gggctgtctg tgaatccgcc tctgccgccc tgcctggcac ccacgctggc tctctcctgc   3000
cgcgggagaa agcaccagca ggttctgagc cctggctgct tgtcctcctc gcaacccccc   3060
caggccggag cttccttcct tagccgggaa gctggcagag gagagccgtg cccgggaata   3120
ggaggaggca gcatgccgag cccctgggac ctcccaggca ggctccggtt ctctcctggg   3180
gactcacggc agcatcgtgg ccaagcaggt gtcggactgc tcagagtccg catggcccag   3240
gagcaggtgg tcggaggccc ctggctttgt gcaaggccgg atctgggcca ggtggcgaaa   3300
ggggcccagt cgttcttggg cccaggatgg ggcctctaga cttgcaaggg agaggaacag   3360
ggaccaggct gccccacggt ccctgaaggg tccaaggagg ggccctcccc atggccctgg   3420
```

-continued

```
agagtgggcc tgggtggtac ctgctccagg cagggaaact gggggctcgc ccttctcctg   3480
tgaggggagc caggcacaca gggcccattg gtgtttggga tgtggacaga ggggcagggg   3540
gctgggagaa ggctaagccg aggggtcctg tttgtgcctc cccttagtcc cttccctccc   3600
gatttcccga ttcccccacc ctccctctac acttgaggac cacagttggg ggtgtaggga   3660
ccacccagac cctggttgaa ttgtttctct ctcctgcttg ttccaaccct tttcactctg   3720
ggcttctccc aaaacccatc ctggcatgac ctgcaactcc aggtggtgga tttgttccaa   3780
agcctcaatc cctaccccct ccaaggggca ggtttccagt ccagcctcag agatcaggct   3840
ctgggacccc tgcctggggg gtggccttca tgcaccagcc acttccgcag gtgctgactc   3900
ccgcactccc tggcattttt tgcagacaag ggcttgggat ggaccctcag ccccatggta   3960
cgccctgccc agtttccaga tgccctgtcc acttacccta ggtagccccc caccccatca   4020
gtgccgagtc cttgtcccta cctccagctt cctccagcct caaaccgcct ctggatctag   4080
ctgtccttct ccgagtggca cgcctgcccc aggatgcccc ctttccctcc cccccatgcc   4140
cagagccccg cctgcctcag cgggtcaggc cttcagaaca ctgccaccca cccagtttta   4200
taatcccgct ccctctccag gcaaccccac ccaccagcct aggcctgctc ctccaccctt   4260
cccgggaggc agccccggga tgctgagagt tggtggaggg gccaggctgg acgcttcccg   4320
tgggagtccc ctccagacct ggctggcccc tgcagccaca gaaaccacga tggcaaaaaa   4380
tctcattggt tctcaaggac taacctgtgg gggaaagcaa tagagacact ctttttctct   4440
cttttttaa agatttattt cttgaaataa taaatatttt attgggatgt ggcggggccg   4500
gacgccggac accagagcgc gggcggcgga gccagcgggc gagagagcgc gcggcgggcg   4560
cgggttgccc tcgtcgagag ccatgggcgc ggcgcggcgc ggggctgagg atcggcgcgg   4620
cccggaggcg ctggggaccg gggcgcgggc ccggggccgc ctttagccgg caccgagggc   4680
gcggggccgg ggatgagggc gcccgccgcg gggagcccgt ctgcgcgccg cggcaccttc   4740
ccgcccagcg agcgagcccg agcaggcaga cgcgcggccg gcggtctggg ggcgcgccgc   4800
ctcccggtcc ccaaaatgtg aagcggggag ggcggagacg cagagacggc ccggccgggc   4860
gccctcgccg ccctccggca gccgcgccgc tccctccgct gcacgcccag gcctgagcag   4920
cgaggccacc gggccgcgcg ctcccagctt cgctcggacg cggcttcggc ccgcagaggg   4980
ttcgtggccc ggacgcggcg agagctgggc ccaggacggt gcgtccggcc tcgcccgcgg   5040
ctgctcgcac caacaagttt gaacaatgat caccgtcaac cccgatggga agataatggt   5100
cagaagatgc ctggtcaccc tgagaccctt tcggcttttt gtcctgggca tcggcttctt   5160
cactctctgc ttcctgatga cgtctctggg aggccagttc tcggcccggc gcctggggga   5220
ctcgccattc accatccgca cagaagtgat gggggggccc gagtcccgcg gcgtcctgcg   5280
caagatgagc gacctgctgg agctgatggt gaagcgcatg gacgcactgg ccaggctgga   5340
gaacagcagt gagctgcacc gggccggcgg cgacctgcac tttcccgcag acaggatgcc   5400
ccctggggcc ggcctcatgg agcggatcca ggctattgcc cagaacgtct ccgacatcgc   5460
tgtgaaggtg gaccagatcc tgcgccacag tctgctcctg cacagcaagg tgtcagaagg   5520
ccggcgggac cagtgtgagg cacccagtga ccccaagttc cctgactgct cagggaaggt   5580
ggagtggatg cgtgcccgct ggacctctga cccctgctac gccttctttg gggtggacgg   5640
caccgagtgc tccttcctca tctacctcag tgaggtcgag tggttctgcc ccccgctgcc   5700
ctggaggaac cagacggctg cccagagggc acccaagccc ctccccaaag tccaggcagt   5760
tttccgaagc aacctgtccc accttctgga cctgatgggc agcgggaagg agtccctgat   5820
```

-continued

```
cttcatgaag aagcggacca agaggctcac agcccagtgg gcgctggctg cccagcgcct   5880
ggcacagaag ctgggggcca cccagaggga ccagaagcag atcctggtcc acatcggctt   5940
cctgacggag gagtccgggg acgtgttcag ccctcgggtc ctgaagggcg ggcccctagg   6000
ggagatggtg cagtgggcgg acattctgac tgcactctat gtcctgggcc atggcctgcg   6060
ggtcacagtc tccctgaagg agctgcagag taacttaggg gtaccgccag gccggggaag   6120
ctgcccgctc accatgcccc tgcccttcga cctcatctac accgactacc acggcctgca   6180
gcagatgaag cggcacatgg gactctcctt caagaagtac cggtgccgaa tcagggtcat   6240
cgacaccttc gggacggaac ctgcgtacaa ccacgaggag tacgccacgc tgcacggcta   6300
ccggaccaac tggggctact ggaacctcaa ccccaagcag ttcatgacca tgtttcctca   6360
taccccgac aactccttca tgggcttcgt gtccgaggag ctcaacgaga cggagaagcg    6420
gctcatcaaa ggcggcaagg ccagcaacat ggccgtggtg tacggcaagg aggcgagcat   6480
ctggaagctc caggggaagg agaagttcct gggcatcctg aacaaataca tggagatcca   6540
tggcaccgtg tactacgaga gccagcggcc ccccgaggtg ccagcctttg tgaagaacca   6600
cggcctctta ccgcagcctg agtttcagca gctgctgcgc aaggccaaac tcttcatcgg   6660
gtttggcttc ccctacgagg gccccgcccc cctggaggcc atcgccaatg gttgcatctt   6720
cctgcagtcc cgcttcagcc cgccccacag ctccctcaac cacgagttct tccgaggcaa   6780
gcccacctcc agagaggtgt tctcccagca tccctacgcg gagaacttca tcggcaagcc   6840
ccacgtgtgg acagtcgact acaacaactc agaggagttt gaagcagcca tcaaggccat   6900
tatgagaact caggtagacc cctacctacc ctacgagtac acctgcgagg ggatgctgga   6960
gcggatccac gcctacatcc agcaccagga cttctgcaga gctccagacc ctgccctacc   7020
agaggcccac gccccgcaga gcccctttgt cctggccccc aatgccaccc acctcgagtg   7080
ggctcggaac accagcttgg ctcctggggc ctggcccccc gcgcacgccc tgcgggcctg   7140
gctggccgtg cctgggaggg cctgcaccga cacctgcctg gaccacgggc taatctgtga   7200
gccctccttc ttccccttcc tgaacagcca ggacgccttc ctcaagctgc aggtgccctg   7260
tgacagcacc gagtcggaga tgaaccacct gtacccggcg ttcgcccagc ctggccagga   7320
gtgctacctg cagaaggagc ctctgctctt cagctgcgcc ggctccaaca ccaagtaccg   7380
ccggctctgc ccctgccgcg acttccgcaa gggccaggtg gccttgggcc agggctgtct   7440
gtgaatccgc ctctgccgcc ctgcctggca cccacgctgg ctctctcctg ccgcgggaga   7500
aagcaccagc aggttctgag ccctggctgc ttgtcctcct cgcaaccccc ccaggccgga   7560
gcttccttcc ttagccggga agctggcaga ggagagccgt gcccgggaat aggaggaggc   7620
agcatgccga gcccctggga cctcccaggc aggctccggt tctctcctgg ggactcacgg   7680
cagcatcgtg gccaagcagg tgtcggactg ctcagagtcc gcatggccca ggagcaggtg   7740
gtcggaggcc cctggctttg tgcaaggccg gatctgggcc aggtggcgaa aggggcccag   7800
tcgttcttgg gcccaggatg gggcctctag acttgcaagg gagaggaaca gggaccaggc   7860
tgccccacgg tccctgaagg gtccaaggag gggccctccc catggccctg gagagtgggc   7920
ctgggtggta cctgctccag gcagggaaac tgggggctcg cccttctcct gtgaggggag   7980
ccaggcacac agggcccatt ggtgtttggg atgtggacag aggggcaggg ggctgggaga   8040
aggctaagcc gaggggtcct gtttgtgcct cccccttagtc ccttccctcc cgatttcccg  8100
attcccccac cctccctcta cacttgagga ccacagttgg gggtgtaggg accacccaga   8160
```

-continued

```
ccctggttga attgtttctc tctcctgctt gttccaaccc ttttcactct gggcttctcc   8220

caaaacccat cctggcatga cctgcaactc caggtggtgg atttgttcca aagcctcaat   8280

ccctacccc tccaaggggc aggtttccag tccagcctca gagatcaggc tctgggaccc    8340

ctgcctgggg ggtggccttc atgcaccagc cacttccgca ggtgctgact cccgcactcc   8400

ctggcatttt ttgcagacaa gggcttggga tggaccctca gccccatggt acgccctgcc   8460

cagtttccag atgccctgtc cacttaccct aggtagcccc ccaccccatc agtgccgagt   8520

ccttgtccct acctccagct tcctccagcc tcaaaccgcc tctggatcta gctgtccttc   8580

tccgagtggc acgcctgccc caggatgccc cctttccctc ccccccatgc ccagagcccc   8640

gcctgcctca gcgggtcagg ccttcagaac actgccaccc acccagtttt ataatcccgc   8700

tccctctcca ggcaacccca cccaccagcc taggcctgct cctccaccct tcccgggagg   8760

cagccccggg atgctgagag ttggtggagg ggccaggctg gacgcttccc gtgggagtcc   8820

cctccagacc tggctggccc ctgcagccac agaaaccacg atggcaaaaa atctcattgg   8880

ttctcaagga ctaacctgtg ggggaaagca atagagacac tctttttctc tcttttttta   8940

aagatttatt tcttgaaata ataaatattt tattgggatg tg                      8982


<210> SEQ ID NO 2
<211> LENGTH: 792
<212> TYPE: PRT
<213> ORGANISM: Homo sapiens

<400> SEQUENCE: 2

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
        35                  40                  45

Arg Leu Gly Asp Ser Pro Phe Thr Ile Arg Thr Glu Val Met Gly Gly
    50                  55                  60

Pro Glu Ser Arg Gly Val Leu Arg Lys Met Ser Asp Leu Leu Glu Leu
65                  70                  75                  80

Met Val Lys Arg Met Asp Ala Leu Ala Arg Leu Glu Asn Ser Ser Glu
                85                  90                  95

Leu His Arg Ala Gly Gly Asp Leu His Phe Pro Ala Asp Arg Met Pro
            100                 105                 110

Pro Gly Ala Gly Leu Met Glu Arg Ile Gln Ala Ile Ala Gln Asn Val
        115                 120                 125

Ser Asp Ile Ala Val Lys Val Asp Gln Ile Leu Arg His Ser Leu Leu
    130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Gln Arg Ala Pro Lys
    210                 215                 220

Pro Leu Pro Lys Val Gln Ala Val Phe Arg Ser Asn Leu Ser His Leu
```

-continued

```
225                 230                 235                 240

Leu Asp Leu Met Gly Ser Gly Lys Glu Ser Leu Ile Phe Met Lys Lys
                245                 250                 255

Arg Thr Lys Arg Leu Thr Ala Gln Trp Ala Leu Ala Ala Gln Arg Leu
            260                 265                 270

Ala Gln Lys Leu Gly Ala Thr Gln Arg Asp Gln Lys Gln Ile Leu Val
        275                 280                 285

His Ile Gly Phe Leu Thr Glu Glu Ser Gly Asp Val Phe Ser Pro Arg
    290                 295                 300

Val Leu Lys Gly Gly Pro Leu Gly Glu Met Val Gln Trp Ala Asp Ile
305                 310                 315                 320

Leu Thr Ala Leu Tyr Val Leu Gly His Gly Leu Arg Val Thr Val Ser
                325                 330                 335

Leu Lys Glu Leu Gln Ser Asn Leu Gly Val Pro Pro Gly Arg Gly Ser
            340                 345                 350

Cys Pro Leu Thr Met Pro Leu Pro Phe Asp Leu Ile Tyr Thr Asp Tyr
        355                 360                 365

His Gly Leu Gln Gln Met Lys Arg His Met Gly Leu Ser Phe Lys Lys
    370                 375                 380

Tyr Arg Cys Arg Ile Arg Val Ile Asp Thr Phe Gly Thr Glu Pro Ala
385                 390                 395                 400

Tyr Asn His Glu Glu Tyr Ala Thr Leu His Gly Tyr Arg Thr Asn Trp
                405                 410                 415

Gly Tyr Trp Asn Leu Asn Pro Lys Gln Phe Met Thr Met Phe Pro His
            420                 425                 430

Thr Pro Asp Asn Ser Phe Met Gly Phe Val Ser Glu Glu Leu Asn Glu
        435                 440                 445

Thr Glu Lys Arg Leu Ile Lys Gly Gly Lys Ala Ser Asn Met Ala Val
    450                 455                 460

Val Tyr Gly Lys Glu Ala Ser Ile Trp Lys Leu Gln Gly Lys Glu Lys
465                 470                 475                 480

Phe Leu Gly Ile Leu Asn Lys Tyr Met Glu Ile His Gly Thr Val Tyr
                485                 490                 495

Tyr Glu Ser Gln Arg Pro Pro Glu Val Pro Ala Phe Val Lys Asn His
            500                 505                 510

Gly Leu Leu Pro Gln Pro Glu Phe Gln Gln Leu Leu Arg Lys Ala Lys
        515                 520                 525

Leu Phe Ile Gly Phe Gly Phe Pro Tyr Glu Gly Pro Ala Pro Leu Glu
    530                 535                 540

Ala Ile Ala Asn Gly Cys Ile Phe Leu Gln Ser Arg Phe Ser Pro Pro
545                 550                 555                 560

His Ser Ser Leu Asn His Glu Phe Phe Arg Gly Lys Pro Thr Ser Arg
                565                 570                 575

Glu Val Phe Ser Gln His Pro Tyr Ala Glu Asn Phe Ile Gly Lys Pro
            580                 585                 590

His Val Trp Thr Val Asp Tyr Asn Asn Ser Glu Glu Phe Glu Ala Ala
        595                 600                 605

Ile Lys Ala Ile Met Arg Thr Gln Val Asp Pro Tyr Leu Pro Tyr Glu
    610                 615                 620

Tyr Thr Cys Glu Gly Met Leu Glu Arg Ile His Ala Tyr Ile Gln His
625                 630                 635                 640

Gln Asp Phe Cys Arg Ala Pro Asp Pro Ala Leu Pro Glu Ala His Ala
                645                 650                 655
```

```
Pro Gln Ser Pro Phe Val Leu Ala Pro Asn Ala Thr His Leu Glu Trp
            660                 665                 670

Ala Arg Asn Thr Ser Leu Ala Pro Gly Ala Trp Pro Pro Ala His Ala
        675                 680                 685

Leu Arg Ala Trp Leu Ala Val Pro Gly Arg Ala Cys Thr Asp Thr Cys
    690                 695                 700

Leu Asp His Gly Leu Ile Cys Glu Pro Ser Phe Phe Pro Phe Leu Asn
705                 710                 715                 720

Ser Gln Asp Ala Phe Leu Lys Leu Gln Val Pro Cys Asp Ser Thr Glu
                725                 730                 735

Ser Glu Met Asn His Leu Tyr Pro Ala Phe Ala Gln Pro Gly Gln Glu
            740                 745                 750

Cys Tyr Leu Gln Lys Glu Pro Leu Leu Phe Ser Cys Ala Gly Ser Asn
        755                 760                 765

Thr Lys Tyr Arg Arg Leu Cys Pro Cys Arg Asp Phe Arg Lys Gly Gln
    770                 775                 780

Val Ala Leu Gly Gln Gly Cys Leu
785                 790


<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide AG

<400> SEQUENCE: 3

Cys Ala Gly Ser Asn Thr Lys Tyr Arg Arg Leu
  1               5                  10


<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide RA

<400> SEQUENCE: 4

Cys Arg Ala Pro Asp Pro Ala Leu Pro Glu Ala His Ala Pro Gln
  1               5                  10                  15


<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide primer derived from Homo sapiens

<400> SEQUENCE: 5

gactagttct agatcgcgag cggccgccct tttttttttt tttt                      44


<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide primer 4470-2043

<400> SEQUENCE: 6
```

-continued

```
agatccatgg caccgtgtac tac                                             23


<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide primer 4470-2230

<400> SEQUENCE: 7

gaagatgcaa ccattggcg                                                  19
```